(12) United States Patent
Stryker et al.

(10) Patent No.: US 10,182,956 B2
(45) Date of Patent: Jan. 22, 2019

(54) TRANSPORT APPARATUS

(71) Applicant: Stryker Corporation, Kalamazoo, MI (US)

(72) Inventors: Martin W. Stryker, Kalamazoo, MI (US); Jason James Wroblewski, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 168 days.

(21) Appl. No.: 15/119,955

(22) PCT Filed: Feb. 13, 2015

(86) PCT No.: PCT/US2015/015755
§ 371 (c)(1),
(2) Date: Aug. 18, 2016

(87) PCT Pub. No.: WO2015/126742
PCT Pub. Date: Aug. 27, 2015

(65) Prior Publication Data
US 2017/0056267 A1 Mar. 2, 2017

Related U.S. Application Data

(60) Provisional application No. 61/941,638, filed on Feb. 19, 2014.

(51) Int. Cl.
*A61G 5/04* (2013.01)
*A61G 7/10* (2006.01)
(Continued)

(52) U.S. Cl.
CPC ............. *A61G 7/1046* (2013.01); *A61G 5/14* (2013.01); *A61G 7/1019* (2013.01);
(Continued)

(58) Field of Classification Search
CPC ................................... A61G 5/04; A61G 5/14
(Continued)

(56) References Cited

U.S. PATENT DOCUMENTS

| 3,107,105 A | 10/1963 | Heriford |
| 3,493,245 A | 2/1970 | Nabinger |

(Continued)

FOREIGN PATENT DOCUMENTS

| CN | 101868215 B | 8/2013 |
| DE | 2749146 A1 | 5/1978 |

(Continued)

OTHER PUBLICATIONS

International Search Report for PCT/US2015/15755, the international counterpart to U.S. Appl. No. 61/941,638.

(Continued)

*Primary Examiner* — Fredrick C Conley
(74) *Attorney, Agent, or Firm* — Warner Norcross + Judd LLP

(57) ABSTRACT

A transport apparatus includes a base, a sling, and a support frame mounted to the base. The frame is configured to move from a first position relative to the base to a second position relative to the base. The frame includes a U-shaped frame with a lower cross-frame member and vertically oriented spaced side frame members joined with the cross-frame member. The side frame members support arm rests, and the cross-frame member optionally forms a footrest. In another aspect, the frame includes an access opening to allow a person egress and ingress to and from the sling through the frame.

20 Claims, 21 Drawing Sheets

(51) Int. Cl.

| | |
|---|---|
| *A61G 5/14* | (2006.01) |
| *A61H 1/00* | (2006.01) |
| *A61H 3/04* | (2006.01) |
| *A61H 23/02* | (2006.01) |
| *A61N 1/36* | (2006.01) |
| *A63B 22/06* | (2006.01) |
| *A63B 22/00* | (2006.01) |
| *A61N 1/04* | (2006.01) |
| *A61G 5/10* | (2006.01) |
| *A63B 71/00* | (2006.01) |

(52) U.S. Cl.
CPC ......... *A61G 7/1051* (2013.01); *A61G 7/1059* (2013.01); *A61H 1/005* (2013.01); *A61H 3/04* (2013.01); *A61H 23/02* (2013.01); *A61N 1/0492* (2013.01); *A61N 1/36003* (2013.01); *A63B 22/0005* (2015.10); *A63B 22/0605* (2013.01); *A63B 22/0694* (2013.01); *A61G 5/1002* (2013.01); *A61H 2201/0107* (2013.01); *A61H 2201/10* (2013.01); *A61H 2201/1633* (2013.01); *A61H 2201/1635* (2013.01); *A61H 2201/5061* (2013.01); *A61H 2230/06* (2013.01); *A61H 2230/207* (2013.01); *A61H 2230/40* (2013.01); *A63B 2071/0072* (2013.01); *A63B 2208/0204* (2013.01); *A63B 2208/0233* (2013.01); *A63B 2220/62* (2013.01); *A63B 2230/06* (2013.01); *A63B 2230/42* (2013.01)

(58) Field of Classification Search
USPC ................................................ 5/81.1 R, 86.1
See application file for complete search history.

(56) References Cited

U.S. PATENT DOCUMENTS

| | | | |
|---|---|---|---|
| 3,888,463 A | 6/1975 | O'Brien et al. | |
| 4,010,499 A | 3/1977 | Davis et al. | |
| 4,070,721 A | 1/1978 | Stasko | |
| 4,157,593 A | 6/1979 | Kristensson | |
| 4,255,823 A | 3/1981 | Boyer et al. | |
| 4,947,497 A | 8/1990 | Marchand | |
| 5,001,789 A | 3/1991 | Schoenberger | |
| 5,112,076 A | 5/1992 | Wilson | |
| 5,255,934 A * | 10/1993 | Wilson | A61G 5/045 |
| | | | 180/907 |
| 5,333,333 A | 8/1994 | Mah | |
| 5,388,289 A | 2/1995 | Casperson | |
| 5,411,044 A | 5/1995 | Andolfi | |
| 5,526,541 A | 6/1996 | Massey et al. | |
| D395,854 S | 7/1998 | Hernandez et al. | |
| 6,092,247 A | 7/2000 | Wilson | |
| D454,998 S | 3/2002 | Czemeres | |
| 6,427,263 B1 | 8/2002 | Lindell | |
| 7,841,611 B2 | 11/2010 | Ivanchenko | |
| 7,845,665 B2 | 12/2010 | Borisoff | |
| 8,336,133 B2 | 12/2012 | Palay et al. | |
| 9,084,710 B2 | 7/2015 | Paul et al. | |
| 2006/0048294 A1 | 3/2006 | Maguire et al. | |
| 2009/0307840 A1 | 12/2009 | Lingegard | |
| 2010/0154115 A1 | 6/2010 | Wernqvist et al. | |
| 2010/0287698 A1 | 11/2010 | Stryker | |
| 2010/0326767 A1 | 12/2010 | Guthrie et al. | |
| 2012/0090089 A1 | 4/2012 | Stryker et al. | |
| 2012/0317715 A1 | 12/2012 | Corriveau et al. | |
| 2015/0190293 A1 | 7/2015 | Hacikadiroglu et al. | |
| 2016/0367420 A1 | 12/2016 | Zerhusen et al. | |

FOREIGN PATENT DOCUMENTS

| | | |
|---|---|---|
| EP | 0932385 B1 | 3/2004 |
| EP | 2536376 | 8/2011 |
| JP | 2001-346839 | 12/2001 |
| NL | 1001881 C2 | 6/1997 |
| WO | 1998007402 A1 | 2/1998 |

OTHER PUBLICATIONS

International Written Opinion for PCT/US2015/15755, the international counterpart to U.S. Appl. No. 61/941,638.
PCT Search Report and Written Opinion dated Apr. 20, 2012 for corresponding PCT Application No. PCT/US2011/052972.
European Search Report for 11834810.0, the European counterpart to U.S. Appl. No. 13/242,494.

* cited by examiner

TRANSPORT APPARATUS

CROSS-REFERENCE TO RELATED APPLICATION

This is a national stage application of PCT/US2015/015755 filed on Feb. 13, 2015, which claims the benefit of U.S. Provisional patent application Ser. No. 61/941,638 filed on Feb. 19, 2014 and relates to U.S. application Ser. No. 12/774,365, filed May 5, 2010, entitled TRANSPORT APPARATUS, by Applicant Martin W. Stryker, and to U.S. application Ser. No. 13/242,494, filed Sep. 23, 2011, entitled TRANSPORT APPARATUS, by Applicant Martin W. Stryker, which are all incorporated by reference herein in their entireties.

BACKGROUND

When people are disabled, aged or injured, mobility can become more difficult, and may need assistance to move or to be transferred between one location or position, for example, on a bed, to another location or position, for example, to a chair.

SUMMARY

A transport apparatus is described that allows a person to move or be transported from one location to another location or transferred from one support to another support. Optionally, the transport apparatus is configured to allow a person to be moved from a supine position or a sitting position on one support, such a bed or seat, to a sitting position or supine position on another support, such as a seat or bed, while reducing the stress or strain on a helper moving the person. Further, the transport apparatus may be used to assist a person to walk. In yet other embodiments, the transport apparatus may be used as a therapy device, such as during rehabilitation. For example, the apparatus may incorporate a lift mechanism to raise or lower the support surface (on which a person is supported) of the apparatus to increase or decrease the load on a patient's appendages, such as legs while standing.

In one form, a transport apparatus includes a set of bearings and a frame mounted relative to the bearings. The frame is configured to move from a first position spaced relative to the bearings to a second position spaced relative to the bearings. The frame includes a U-shaped frame with a lower cross frame member and spaced side frame members joined with the cross-frame member. The side frame members support one or more arm rests.

In one aspect, the lower cross-frame member forms a footrest.

In another aspect, the frame supports seat support members configured to support a sling. For example, the seat support members may be releasably engageable with a sling.

According to yet another aspect, the transport apparatus includes a sling. For example, the sling may include a seat portion and/or a back portion. Optionally, the sling includes both a seat portion and a back portion. Further, the seat portion and back portion may be connected together and reconfigurable between an unfolded, generally planar configuration, wherein the sling can lie generally flat on a support surface so that a person may be moved onto the sling, and a folded configuration wherein a person can be supported in a sitting position on the sling.

Optionally, the seat portion is releasably engageable with the seat support members of the frame, with the back portion releasably engageable with the arm rests. In a further aspect, the seat support members may be releasably joined with the arm rests.

In another aspect, the arm rests are formed by the side frame members.

According to yet another aspect, the side frame members form an access opening there between. The access opening is configured to allow egress and ingress through the access opening at least when the frame is in its first position.

In a further aspect, the seat support members are joined with the arm rests.

In another aspect, the sling includes an opening to allow a user to use a commode without the removal of the sling. Further, the sling may be disposable.

In any of the above, the first position may be higher than the second position.

In any of the above, the U-shaped member includes spaced apart side frame members with lower portions and upper portions, with the upper portions angled or curved relative to the lower portions. The upper portions optionally form or support the arm rests.

According to yet another form, a transport apparatus includes a base with bearings, first and second spaced apart seat support members configured to support a seat for supporting a person thereon, and a frame mounted relative to the base. The frame is configured to move from a first position relative to the base to a second position spaced from the base different than the first position. The frame is configured to support seat support members and to form an access opening, with the access opening configured to allow egress and ingress to and from the seat through the access opening at least when the frame is in the first position.

In one aspect, the seat support members support a sling, which forms the seat. For example, the sling may include a seat portion and a back portion, with the seat portion and the back portion connected together and reconfigurable between an unfolded generally planar configuration, wherein the sling can lie generally flat on a first support surface so that a person may be moved onto the sling, and a folded configuration, wherein a person can be supported in a sitting position on the sling.

In another aspect, the seat support members are engageable by the seat portion for engaging the sling. Further, the back portion may be releasably engageable with the frame to hold the sling in its folded configuration.

According to yet a further aspect, the support frame is further configured to move to a third position relative to the base.

In one aspect, the second position is spaced further from the base than the first position.

In another form, a transport apparatus includes bearings and a frame mounted relative to bearings. The frame is configured to move between a first position spaced relative to the bearings to a second position relative to the bearings different than the first position. The frame is configured to support a seat that comprises a flexible panel forming a seat portion and a back portion and which is reconfigurable between an unfolded, generally planar configuration wherein the panel can lie generally flat on a support surface so that a person may be moved onto the panel, and a folded configuration where the person may be supported in a sitting position on the panel. The frame has spaced side frame members between which the panel is supported. The side frame members are spaced sufficiently to allow a person to egress and ingress to and from the seat portion between the side frame members when the frame is in its first position.

According to one aspect, each of the side frame members supports a mount for releasably sliding the seat portion onto the side frame members.

In another aspect, portions of the side frame members form arm rests. For example, the arm rests may be configured to support handles.

According to yet another aspect, the arm rests, the mounts, the side frame members form closed loops to thereby retain the seat on the transport apparatus. For example, each of the arm rests and each of the mounts may be joined by a releasable link. When released, the links open the closed loops formed by the arm rests, mounts and side frame members, to thereby allow the panel to be removed from the frame.

In yet another aspect, the seat portion includes a pair of sleeves, with the mounts being extendable into the sleeves to thereby releasably engage the sling.

According to yet another aspect, the base includes forward bearings and rearward bearings with the frame mounted between the forward bearings. Further, the forward bearings and the rearward bearings define a footprint, with the sling or panel optionally supported within the footprint.

According to yet another form of the invention, a transport apparatus includes a movable base, a sling, which has a seat portion reconfigurable between a generally planar configuration and a cradle configuration, and a frame mounted to the base and releasably engageable with the sling. The frame is configured to allow egress and ingress to and from the seat portion through the frame when the sling is engaged with the frame.

One aspect, the seat portion includes a pair of sleeves, with the frame having support members. The support members are extendable into the sleeves to thereby mount the sling to the frame.

In any of the above, the frame may include at least one driver for raising the frame relative to base or bearings.

In any of the above, the apparatus may include a foot rest. For example the footrest may be supported by the frame.

In any of the above, the apparatus may include a platform, including a platform that is configured to vibrate to provide vibration therapy, for example.

In any of the above, the apparatus may include one or more electro-stimulation devices to apply electro-stimulation therapy to a person supported by the apparatus.

These and other objects, advantages, purposes, and features of the invention will become more apparent from the study of the following description taken in conjunction with the drawings.

DETAILED DESCRIPTION OF THE PREFERRED EMBODIMENT

Figure 1:
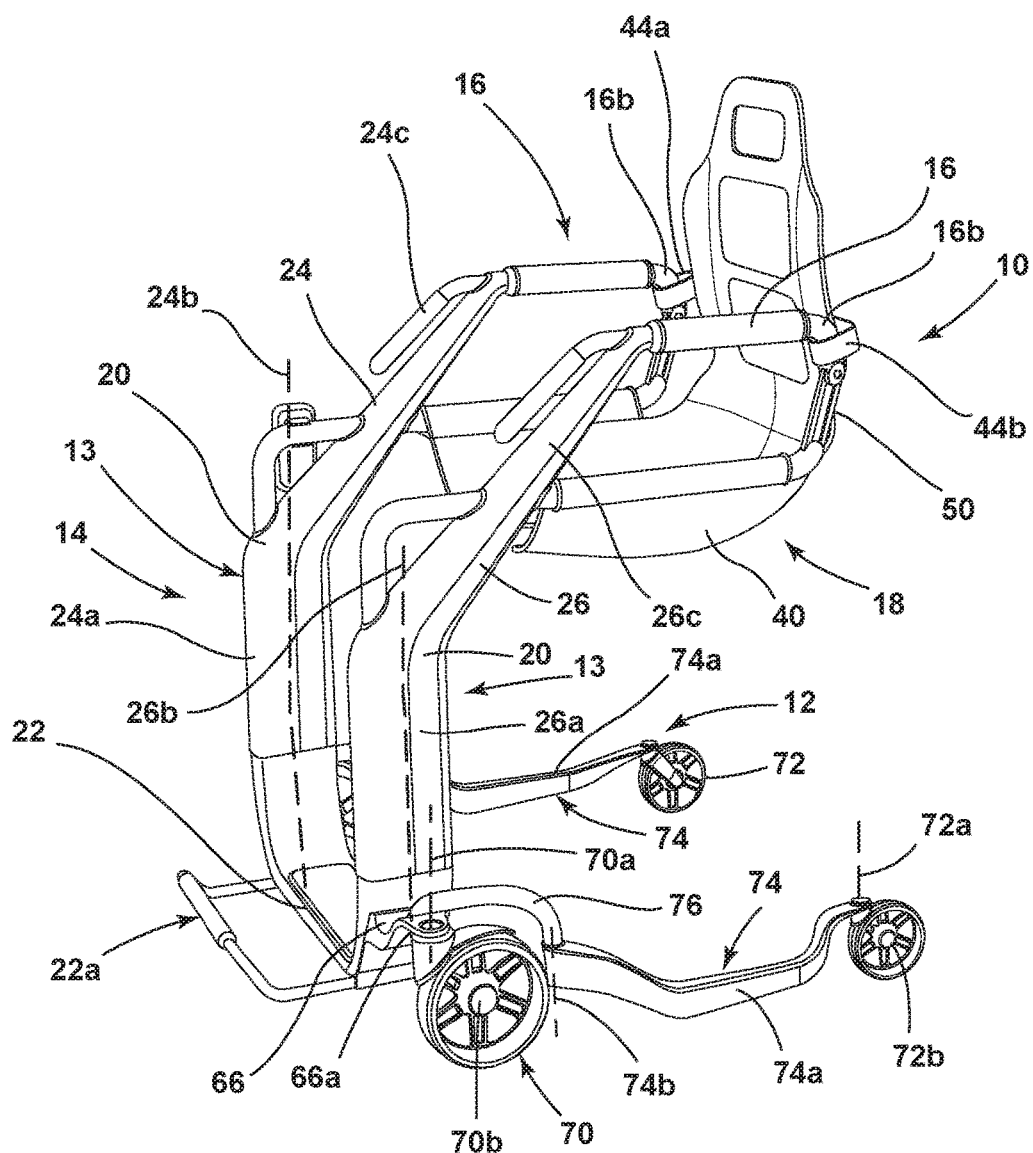
FIG. 1 is a front perspective view of a transport apparatus.

Referring to FIG. 1, the numeral 10 generally designates a transport apparatus. As will be more full described below, transport apparatus 10 facilitates transport of a person and, optionally, allows a person to be transferred or moved, for example, from a supine position or a sitting position on one surface, such as a bed or chair, to a sitting position or supine position on another surface, such as a chair or bed, while reducing the stress or strain on a helper, such as a caregiver, who is moving the person. In addition, apparatus 10 is optionally adapted to be reconfigured as a walker to assist a person to walk and to become more self-mobile. In yet other embodiments, transport apparatus 10 may be used as a therapy device, such as during rehabilitation. For example, as will be more fully described below, apparatus 10 may incorporate a lift mechanism to raise or lower the support surface (on which a person is supported) of the apparatus to increase or decrease the load on a patient's appendages, such as legs while standing. It should be understood that the term "transport" is used broadly and when used in reference to a transport apparatus includes apparatuses that allow a person to be moved from one location or position to another location or position, or just simply to be supported.

As best seen in FIG. 1, transport apparatus 10 includes a base 12 and spaced columns 13 that are supported by base 12. Columns 13 form a support frame 14 that supports arm rests 16 and, optionally, a seat 18, which provide one or more support surfaces on which a person can be supported. Seat 18 is cantilevered over and spaced relative to base 12 so that base 12 and frame 14, and seat 18 when mounted, have a generally C-shaped configuration (when viewed from the side of the apparatus (FIG. 1)). Support frame 14 is movably mounted to base 12 so that it can be moved relative to base 12, for example, raised or lowered, to allow the seat and/or arm rests to be moved to either allow a person to be transferred from one support to another support or be reconfigured from a carrying function to a walker function, or to provide seating, for example, with an adjustable height. Further, as will be more fully described below, apparatus 10 may incorporate a lift mechanism, including a powered lift mechanism, that raises or lowers support frame 14 relative to base 12.

As best seen in FIGS. 5-9, support frame 14 is configured to allow egress and ingress to and from the seat. For example, in the illustrated embodiment, frame 14 is configured to provide an egress or ingress path between columns 13 through the frame (at least when the frame is in one of its positions). This allows a person to climb out of the seat or climb into the seat to seat themselves on the seat, while still providing support to seat 18 and arm rests 16 and also adjustment to the height of the seat and/or the arm rests. The path to and from the seat is, therefore, free of any obstructions, at least when a person wishes to have egress from or ingress to the seat. As will be described below, the columns may be selectively, temporarily joined together to provide increased stability.

Referring again to FIG. 1, in the illustrated embodiment, support frame 14 includes a U-shaped frame 20 with a lower cross-frame member 22 and side frame members 24 and 26. Side frame members 24 and 26 form columns 13 for supporting arm rests 16 and seat 18, more fully described below. Lower cross-frame member 22 is positioned below the egress and ingress path and may form a footrest. An optional extended foot rest in the form of a U-shaped tubular frame 22a may also be provided and mounted at or beneath cross-frame member 22. For example, in the illustrated embodiment, the ends of tubular frame 22a are mounted in tubular sleeves provided beneath or formed at the underside of cross-frame member 22. Optionally, as described in reference to another embodiment, the cross-frame member may be eliminated. Further, as would be understood, the construction and/or shape of the extended footrest can be varied.

Frame members 24 and 26 are spaced apart a distance to form the access opening there between. Frame member 24, 26 have lower or first portions 24a, 26a, respectively, which are generally parallel and further optionally extend along vertical axes 24b, 26b to accommodate the movement of frame relative to base 12, more fully described below. Frame members 24 and 26 also have upper or second portions 24c and 26c. Optionally, second positions 24c and 26c are configured so that seat 18 is positioned rearward of lower portions 24a, 26a and/or so that the arm rests 16 are rearward of lower portions 24a, 26a. For example, second portions 24c and 26c may be angled or curved with respect to lower portions 24a, 26a. The terms "rearward" or "forward" as used herein are used as directional terms indicating a direction relative to the direction the person is a facing when supported by the transport apparatus. In other words, when a person is seated in the transport apparatus the person's face is facing in a forward direction, and their back faces in a rearward direction. The terms are not intended to be limiting and are used merely as reference terms.

Figure 10:
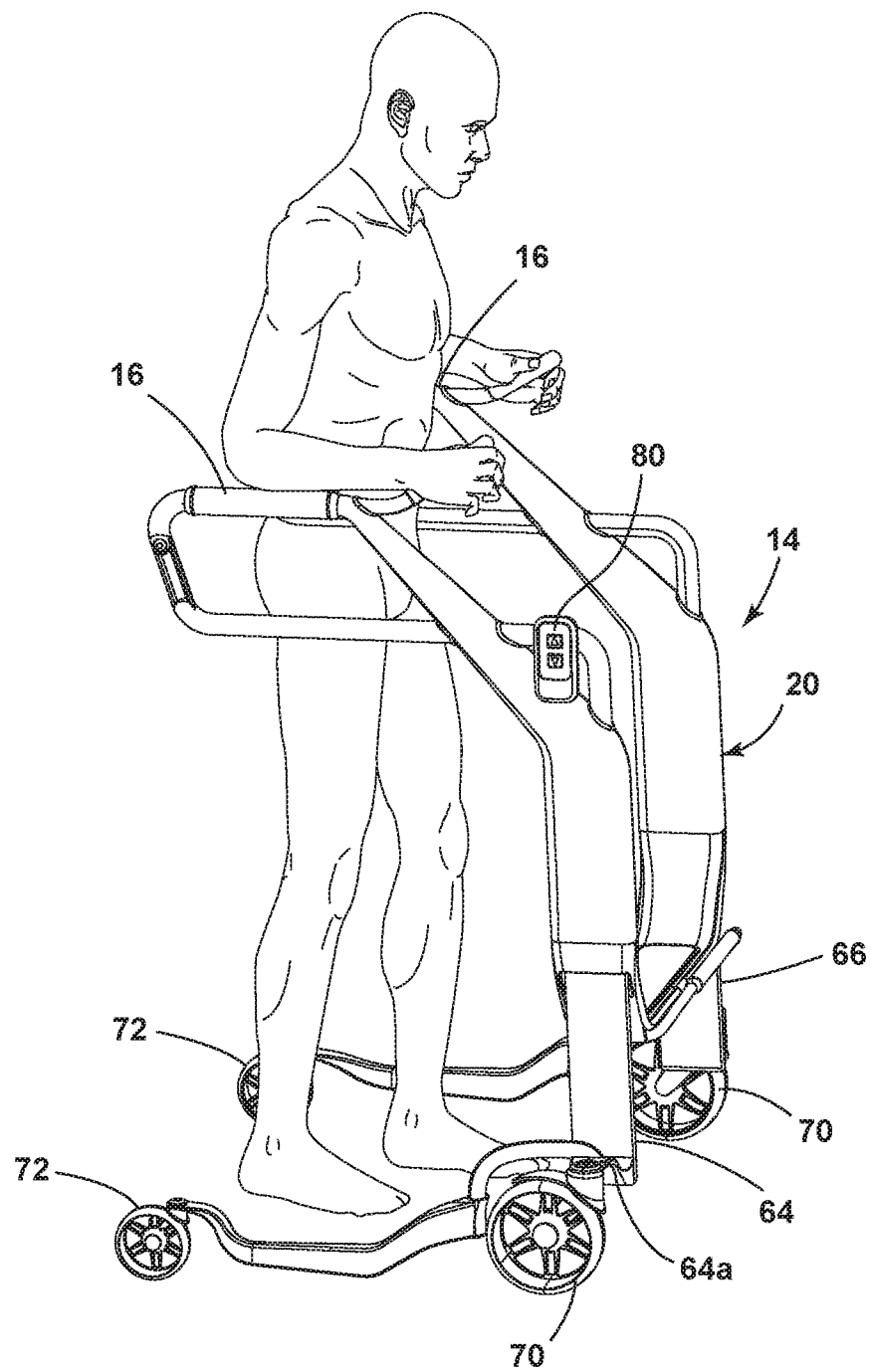
FIG. 10 illustrates the transport apparatus with the sling removed and the arm rests positioned at a height suitable for use as a walker.

Formed on or mounted to the distal ends of upper portions 24c and 26c are the arm rests 16. For example, arm rests 16 may be formed by extensions of upper portions 24c and 26c or may be formed from tubular members that are mounted to the distal ends of upper portions 24c and 26c. Each arm rest 16 may include a compressible outer layer 16a to provide cushioning for comfort and also to provide a gripping surface for the arm rests, for example, when apparatus 10 is used as a walker, such as shown in FIG. 10.

Figure 2:
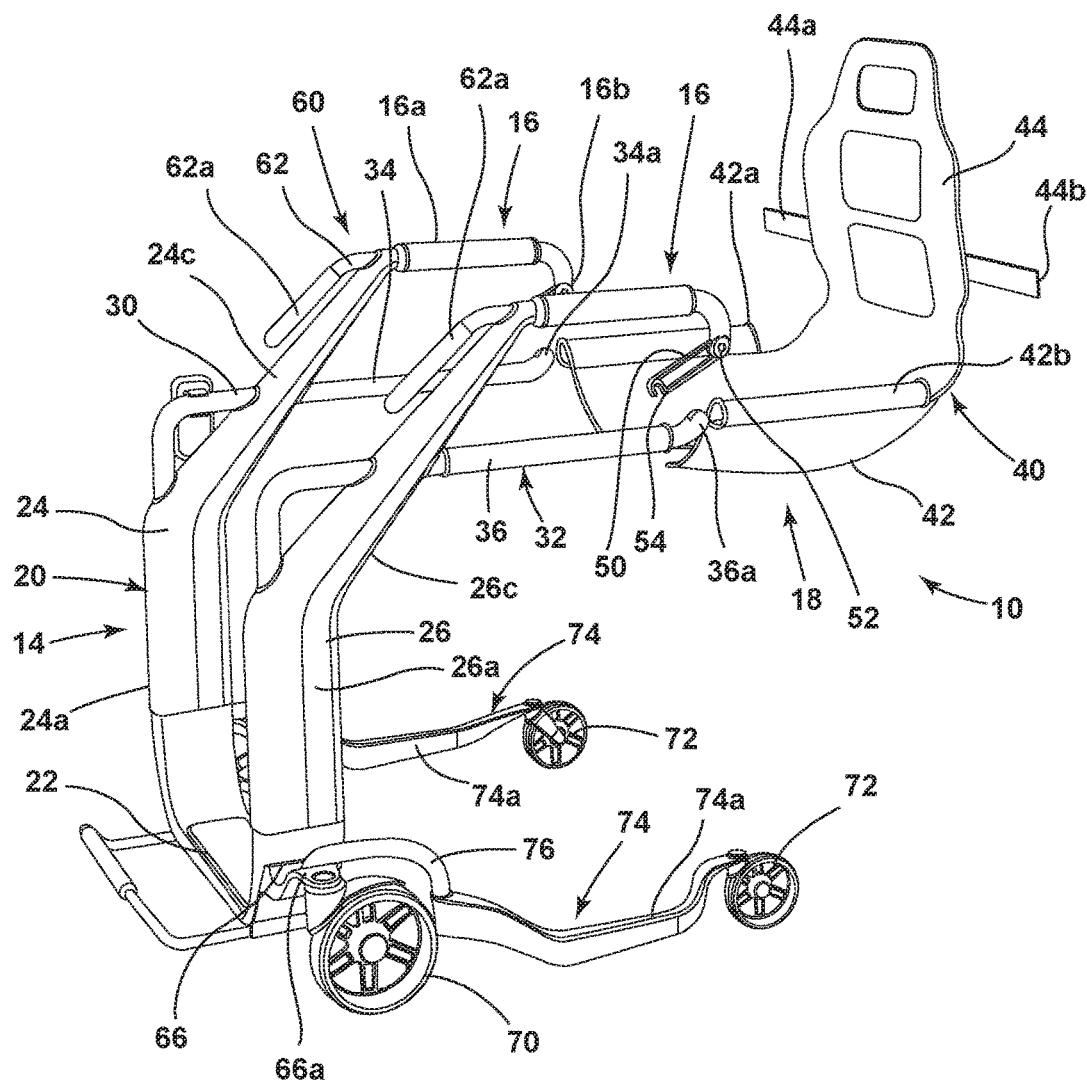
FIG. 2 illustrates the support frame and the sling of the transport apparatus removed.
Figure 3:
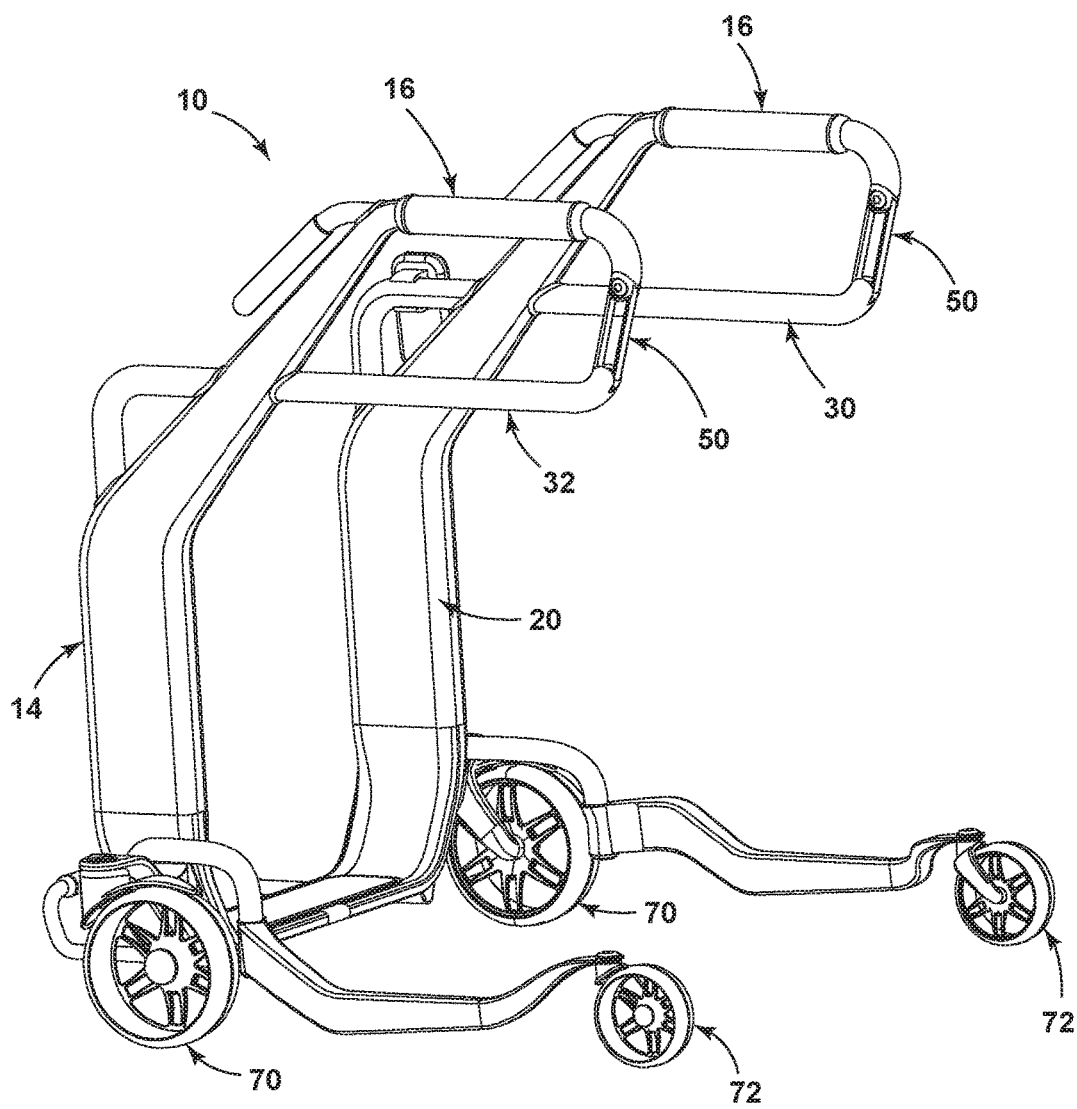
FIG. 3 is rear perspective view of the transport apparatus with the sling removed for clarity.

As best seen in FIG. 2, frame 14 supports a pair of seat mounting members 30 and 32. In the illustrated embodiment, mounting members 30 and 32 comprise L-shaped tubular members 34 and 36 that are anchored at one end to the lower ends of upper portions 24c and 26c and extend through and are supported at their medial portions in the medial portions of upper portions 24c and 26c. The remaining portions of tubular members 34 and 36 project rearwardly from upper portions 24c and 26c in a cantilevered manner from the medial portions of upper portions 24c and 26c so that their distal ends 34a and 36a are free to mount seat 18 to apparatus 10. Optionally, distal ends 34a and 36a may be coupled to the distal ends 16b of arm rests 16 so that after seat 18 is mounted to seat mounting members 30 and 32, the distal ends of seat mounting members 30 and 32 be supported at their distal ends, and further form a closed loop with arm rests 16 and upper portions 24c and 26c. The seat 18 may, therefore, be captured and retained on frame 14 by the frame configuration.

In the illustrated embodiment, seat 18 is formed by a sling 40. Sling 40 includes a panel of flexible material, which as noted may be removably mounted to frame 14. Sling 40 forms a seat portion 42 and a back portion 44, which may be formed from the same panel so that they form a unitary support. Further, optionally sling 40 is configured so that it can be reconfigured between a generally planar arrangement in which the sling may be laid generally flat on a support, such as a bed B, or reconfigured into its folded configuration, such as shown in FIGS. 1 and 2 to support a person in a sitting position, described more fully below. Alternately, the seat portion and back portion may be formed from two panels of material that are connected together, for example, by stitching or the like. The panel or panels may be formed from a flexible material, such as a fabric, including a breathable or gas permeable fabric to provide enhanced air circulation to the person supported by the sling. For example, a suitable fabric may include Gortex or the like. Optionally, the seat and back sections can be formed from separate panels that are not joined together.

Referring again to FIG. 2, sling 40 is releasably mounted to frame 14 on spaced apart seat mounting members 30 and 32. Optionally, the opposed sides of seat portion 42 include closed loops or sleeves 42a and 42b, which are sized to receive seat mounting members 30 and 32. For example, sleeves 42a and 42b may be slid onto the distal ends (when disconnected from arm rests 16) of seat mounting members 30 and 32. In the illustrated embodiment, back portion 44 similarly includes loops 44a and 44b that are sized to extend around the distal end 16 of arm rests 16. For example, loops 44a and 44b may be sized to be slid onto the ends of distal ends of arm rests 16 when distal ends of arm rests 16 are disconnected from the distal ends of seat mounting members 30 and 32 or they may be secured in place by fasteners, such as VELCRO strips, zippers, fasteners, boltropes, or snaps.

As best seen in FIGS. 1 and 2, optionally mounted to each distal end 16b of arm rest 16 is a link 50. Each link 50 is pivotally mounted at its proximal end to a respective distal end 16b of a respective arm rest 16 by pin 52. The opposed end of each link includes a hook 54, such as a C-shaped hook, for engaging a transverse pin (not shown) located in the bifurcated ends of mounting members 30 and 32. In this manner, when each link 50 is pivoted to engage an end of a respective mounting member 30 or 32, each link 50, arm rest 16, mounting member 30 or 32, and side frame member 24 or 26 form a closed loop, which facilitates retention of seat 18 on the apparatus 10, as noted above.

Alternately, one or both sets of loops or sleeves 42a and 42b and 44a and 44b may be formed as a strip and include release mechanisms or fasteners (e.g. Velcro strips or snaps) to allow them to be opened and then mounted about the respective portions of seat mounting member 30 and 32 and/or arm rests 16 and then secured in place, which could eliminate the need for the releasable connection formed by links 50. Thus, when the respective loops of the sling are mounted to frame 14, the sling forms a seat for supporting a person in a sitting position, as well as a back support.

In the illustrated embodiment, frame 14 is formed from a metal tubular member with a rounded rectangular cross-section, which is formed into the U-shaped frame 20. Arm rests 16 and mounting members 30 and 32 may be formed from round tubular metal members, which are then welded to frame 20. Optionally mounted to frame 20 are a pair of handles 60. Handles 60 may also be formed from round tubular metal members 62 that are formed into an inverted L-shape so that the lower portion of the handle, which may also be covered with a compressible material, such as a rubber or rubber like material, can facilitate gripping. Further, handles 60 may be mounted so that they can be repositioned. For example, handles 60 may be rotatably mounted in frame 14 so that the lower portion of the handles may be repositionable between a downward angled orientation, so that they generally follow the angle of upper portions 24c and 26c of side frame members 24 and 26 when not in use, or an upwardly or inwardly angled orientation when in use (see FIG. 10).

As would be understood, being constructed of a tubular member or members, frame 14 may therefore be hollow. This can provide housing for one or more components. In the illustrated embodiment side frame members 24 and 26 of frame 20 provide housing for one or more drivers to raise or lower frame 14 relative to base 12, as well as any supporting wiring and circuitry.

As best understood from FIG. 10, frame 14 is movably mounted to base 12 by way of members 64 and 66 that form part of base 12. In the illustrated embodiment, members 64 and 66 extend from base 12 into frame 14 through openings provided at the ends of frame 14 to thereby form telescoping columns with side frame members 24 and 26. In the illustrated embodiment, members 64 and 66 are not joined together; however as will be described below, members 64 and 66 may be joined by a cross frame member.

Optionally, members 64 and 66 are sized so that they are generally commensurate in size with the hollow space in side frame members 24, 26 of the frame so that members 64 and 66 and frame 14 (specifically lower portions 24a and 26a) form telescoping column members that guide the movement of frame 14, e.g., up or down relative to base 12 and/or its bearing members. Optionally, low friction spacers, such as Teflon spacer bearings, are provided between the inner and outer members that form the telescoping columns to provide a close, but low friction fit between the telescoping members.

In the illustrated embodiment, base 12 comprises a movable base with forward bearings 70 and rearward bearings 72. Further in the illustrated embodiment, bearings 70 comprise wheels, which are rotatably mounted to base 12 about a generally horizontal axis 70b (e.g. by shafts and yokes) and about a generally vertical axis 70a to allow steering. In the illustrated embodiment, bearings 72 also comprise wheels that are mounted about a vertical axis 72a as well as a horizontal axis 72b (e.g. by shafts and yokes) and are spaced from bearings 70 to provide stability to transport apparatus 10. In the illustrated embodiment, bearings 72 are mounted to the rearward side of base 12 and, further, may have a low profile so that base 12 and bearings 72 may be extended under a support, e.g. a bed or other support or apparatus, while seat 18 is extended over the support to place or retrieve a person on the support. Further, base 12 may be configured to locate bearings 72 outside the footprint of seat 18, which can increase the stability of the transport apparatus.

Alternately, the bearings may comprise casters, wheels, low friction pads or skids, air bearings, or the like or a combination of different types of bearings. An example of a suitable low profile bearing is described in U.S. Pat. No. 7,441,786, entitled CONVERTIBLE LOW PROFILE ROLLER AND SUPPORT BASE, issued Oct. 28, 2008, which is incorporated by reference herein in its entirety and commonly owned by Stryker Corporation of Kalamazoo, Mich.

Figure 4:
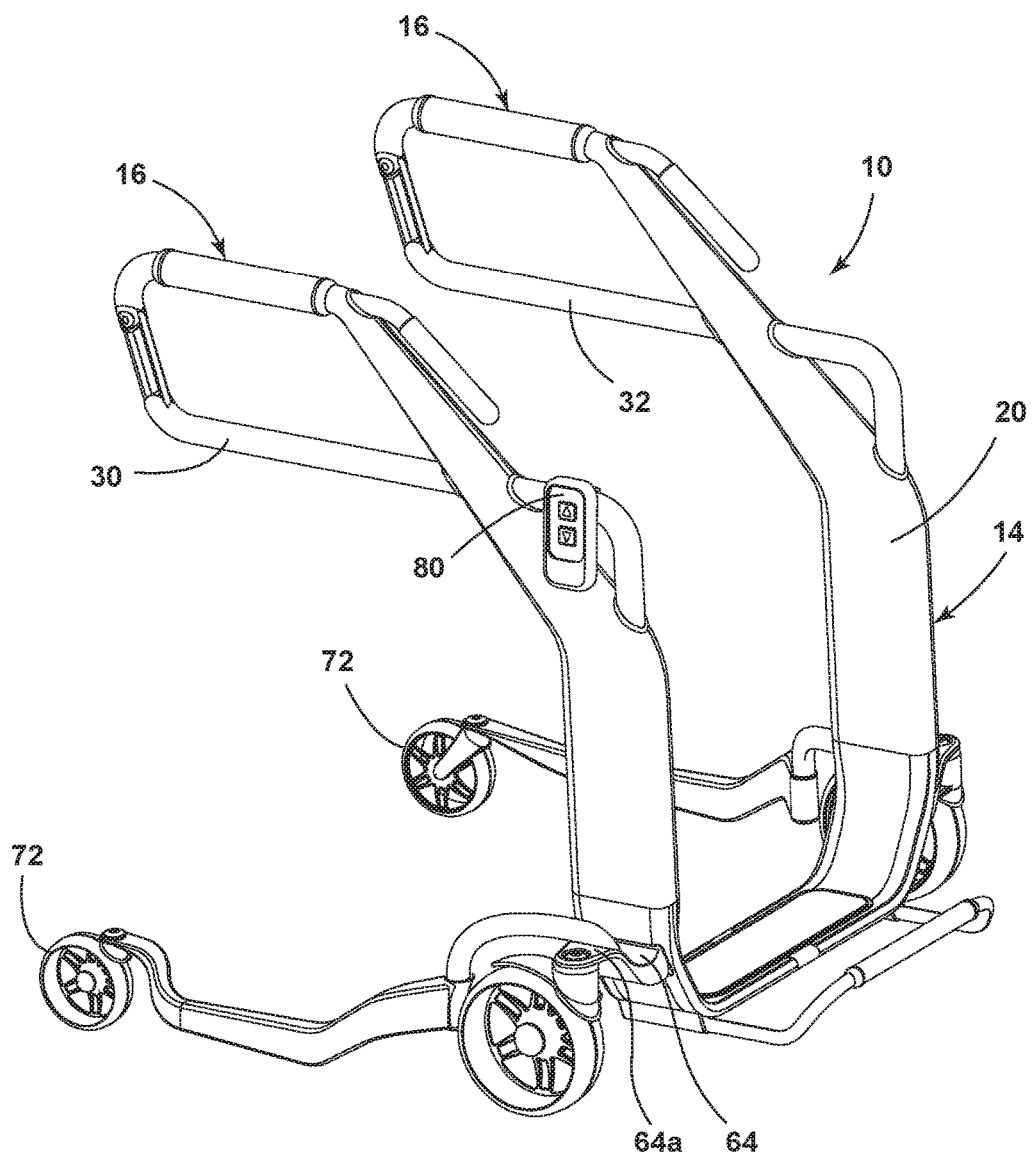
FIG. 4 illustrates a control unit mounted to the transport apparatus.
Figure 5:
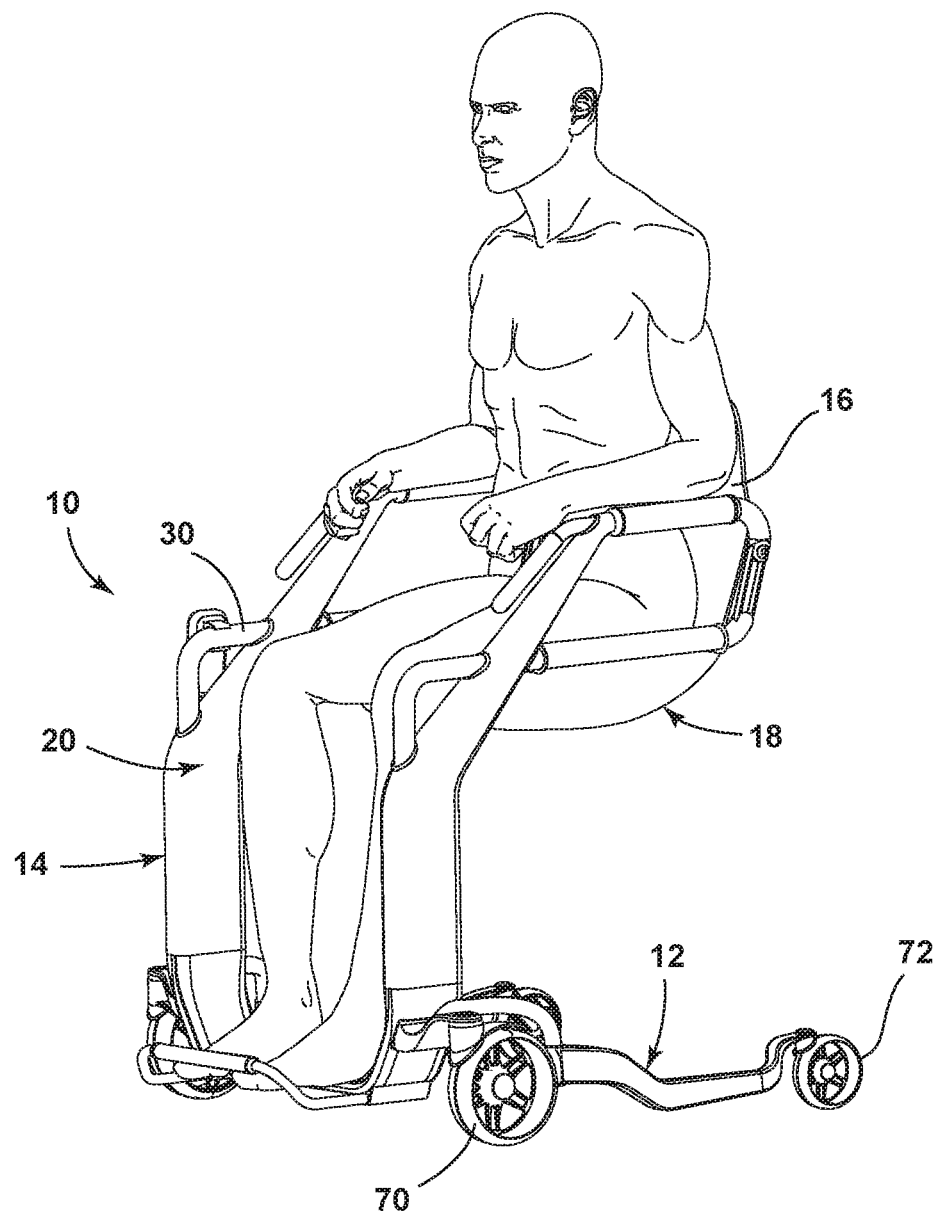
FIG. 5 illustrates the transport apparatus supporting a patient.

As best seen in FIGS. 2, 4, and 10, forward bearings 70 are rotatably mounted to base members 64 and 66 by mounting flanges 64a and 66a. Rearward bearings 72 are rotatably mounted to base frame members 74, which are respectively mounted to mounting flanges 64a and 66a by arms 76. Arms 76 are configured, such as for example by being contoured or bent, to extend up and over wheels 70 and to provide sufficient clearance to allow bearings 70 to pivot about their vertical axes 70a to facilitate steering. Similarly, each base frame member 74 includes an offset portion 74a to increase the space between the two base frame members 74 at least over a portion of their length, which provides increased area for a person's feet when apparatus 10 is used as a walker.

Figure 11A:
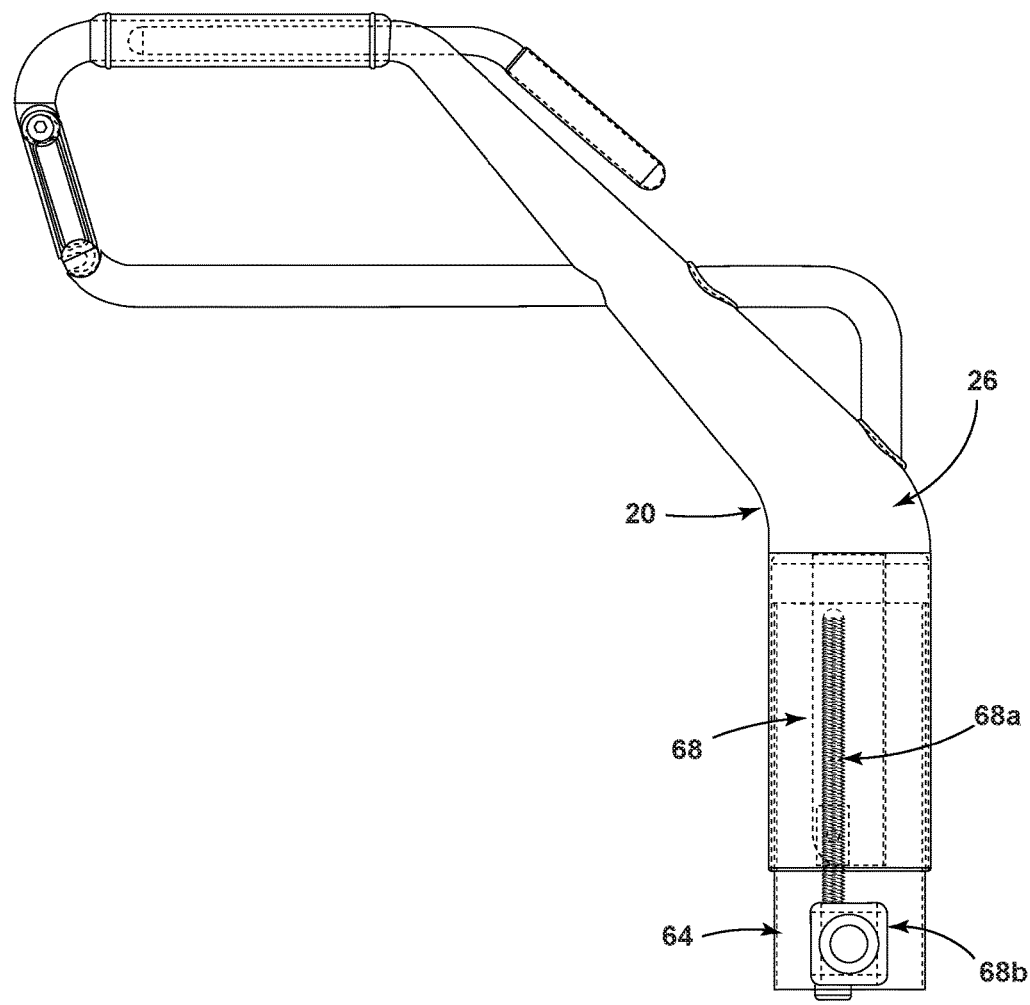
FIG. 11A is a partial fragmentary view of the frame illustrating one embodiment of a driver that moves the frame relative to the base.

Optionally, to move, for example, raise frame 14 relative to bearings 70 and 72, as noted, frame 20 houses one or more lift mechanisms 68 (FIG. 11A). Exemplary lift mechanisms comprise powered lift mechanisms and include a driver in the form of a drive screw assembly or a servo motor or a cylinder with a drive element (e.g. output shaft or screw) that may be coupled to the upper end of a respective member 64, 66 so that when the driver is energized, the driver will push or pull on a respective member 64, 66 to thereby move, for example raise or lower, frame 14 relative to bearings 70, 72 and relative to base 12. Further, optionally frame 20 provides housing for a power supply, such as a battery, including a rechargeable battery. The power supply may be locally controlled to deliver power to the driver or drivers by a local control unit 80, such as shown in FIG. 10, which may be electrically coupled to the battery. Alternatively or in addition, the power supply may include a circuit board mounted in frame 20, which includes a receiver and is configured to selectively deliver power to the drivers in response to input signals. Signals may be electric signals or wireless signals from control unit 80 or wireless signals from a remote control unit (not shown).

As best seen in FIGS. 11A-11D, in the illustrated embodiment, lift mechanism 68 includes a driving element 68a, such as for example, a screw, such as an ACME screw, which is mounted to frame 14. Driving element 68a is driven to rotate by a motor 68b, which is mounted in base 12, such as in member 64. The motor 68b may be powered, as noted, by an on-board power supply, such as an on-board battery, including a rechargeable battery, or may be powered by a remote power supply, for example, by power cord from a standard outlet. Optionally, motor 68b is controlled by the control unit described above.

Figure 11B:
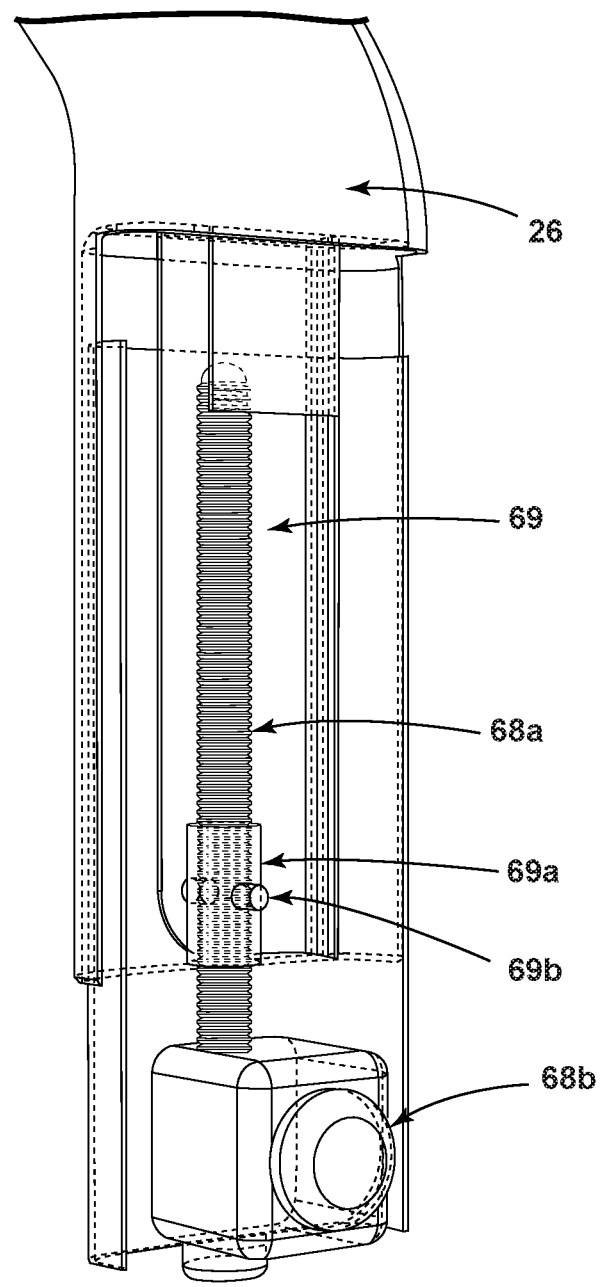
FIG. 11B is an enlarged partial fragmentary view of the frame illustrating the driver of FIG. 11A.
Figure 11C:
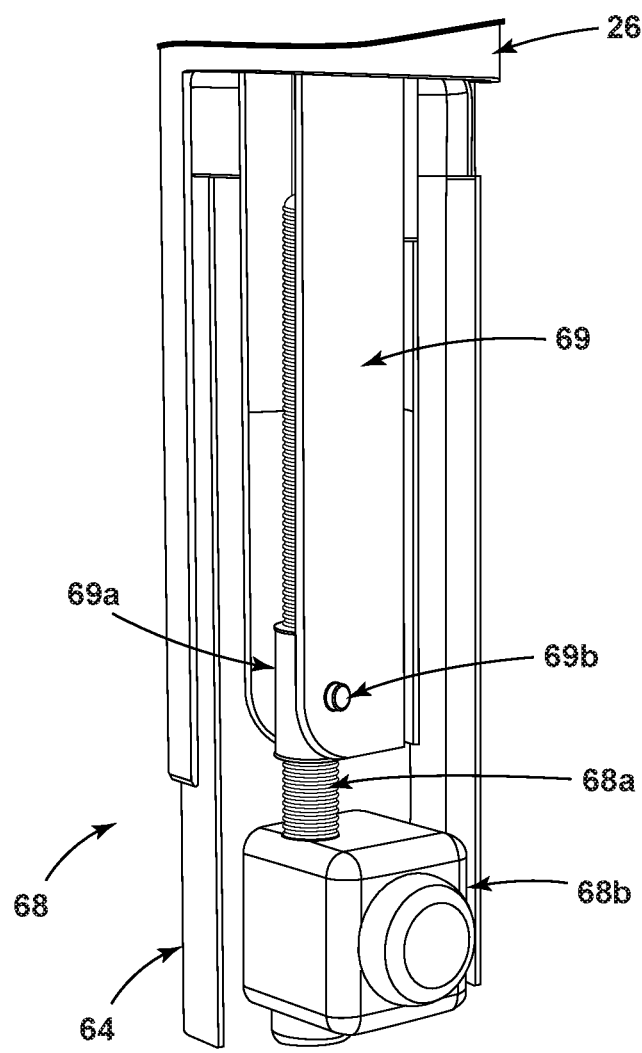
FIG. 11C is another enlarged partial fragmentary illustrating the mounting of the driver of FIG. 11A.
Figure 11D:
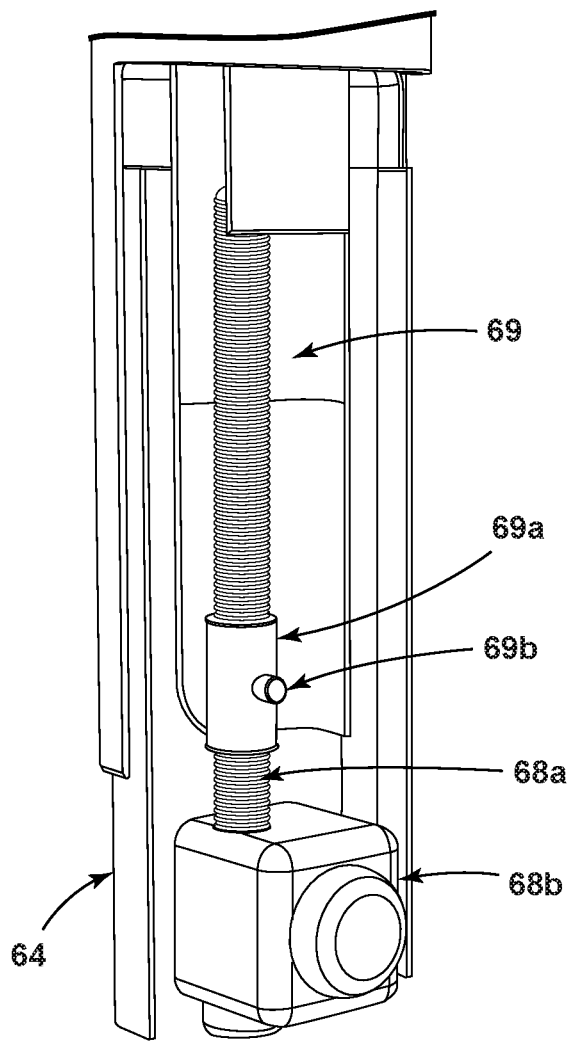
FIG. 11D is another enlarged partial fragmentary view of the driver of FIG. 11A.

Referring to FIG. 11B, each side frame member 24, 26 may include internal tubular members or channels members 69 to which driving element 68a is mounted. For example, driving element 68a may be mounted to member 69 by a bracket. As noted above, one suitable driving element comprises a screw. A suitable bracket, therefore, may include a gimbal mount 69a, which includes a threaded collar that engages the threads of the screw and a pin 69b that mounts the collar between the opposed flanges of member 69. In this manner when motor 68 drives the screw to rotate, the collar will translate the rotary motion of the screw into linear movement, for example linear vertical movement, of member 69 and, in turn, of member 64. As noted above, transport apparatus 10 optionally includes more than one driver. For example, a driver may be provided for each side frame member, or a single driver may be provided in one side frame member with the other side frame member comprising a driverless side frame member but which either forms a guide by its close fit with the base members (64 or 66) or has a guide inside. For example, a suitable guide may include a rod anchored on one end to the base, which extends into the driverless side frame member, and a collar mounted and fixed to the inside of the driverless side frame member. The rod may be extended through the collar with a sliding connection so that the collar can be guided along the rod when the driven side frame member is moved by the driver, to thereby guide the driverless side frame member along the rod.

Figure 6:
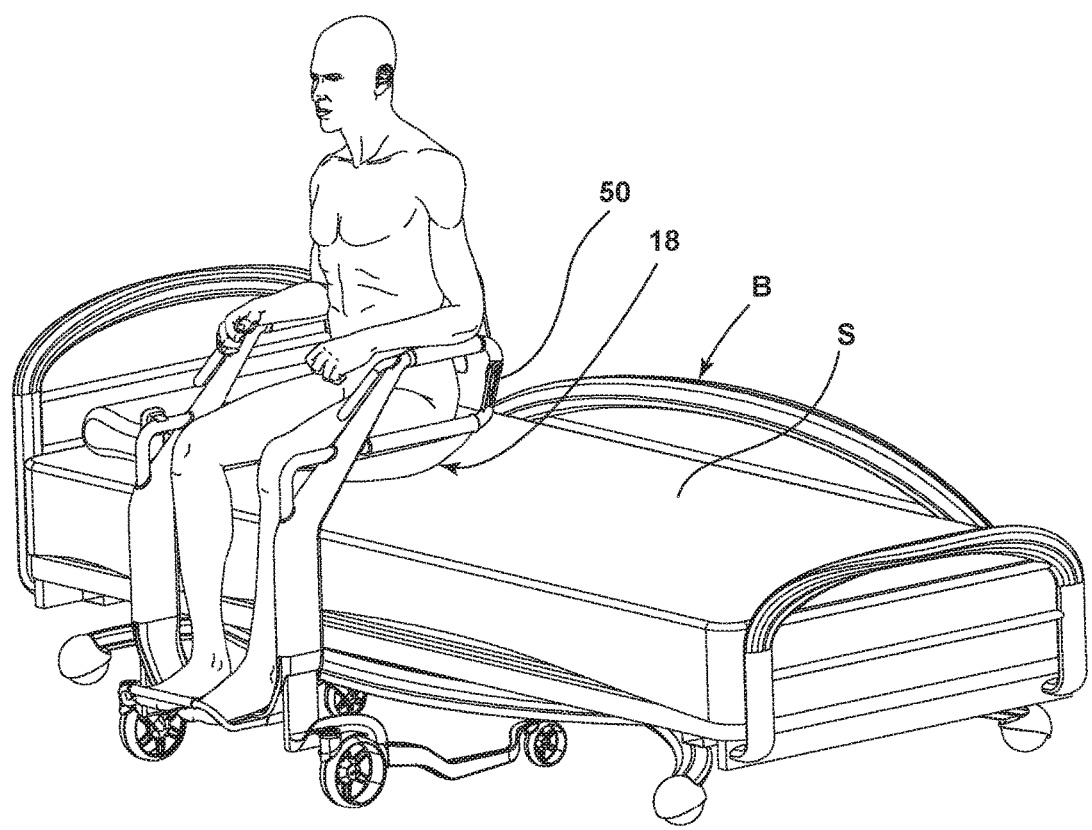
FIG. 6 illustrates the frame and the sling positioning the person over a support, such as a bed.

As best understood from FIGS. 1, 2, and 4, lower portions 24a, 26a of side frame members 24 and 26 are located between bearings 70 and further are generally aligned along axes 70a of bearings 70. Further, upper portions 24c and 26c of side frame members 24 and 26 are configured, as noted, to locate seat 18 between bearings 72 and bearings 70 so that seat 18 is within the footprint defined by bearings 70,72. Optionally as noted, bearings 72 have a smaller diameter to form a lower profile than bearings 70 so that bearings 72 may be positioned, such as by rolling, to extend under a support, such as a bed B, as shown in FIG. 6. In this manner, when apparatus 10 is moved adjacent a support, and bearings 72 are extended under the support, seat 18 can be positioned over the support to allow the person to be deposited on the support.

For example when a person is positioned over the support surface S of a support, such as a mattress of a bed B, coupler 50 may be disengaged from seat mounting members 30 and 32 to allow the back portion 44 of sling 40 to be disengaged from arm rest 16 so that the sling that may be arranged in a generally planar configuration. In a planar configuration, a person may be transferred, for example, by rolling, onto or off the sling. Alternately, loops 44a and 44b of back portion 44 may be opened up to allow back portion 44 to be disengaged from apparatus 10. Thereafter apparatus 10 can be pulled away so that seat mounting members 30 and 32 can disengage from seat portion 42 of sling 40 to allow the person to be deposited on the support surface S and optionally thereafter rotated to a position so that the person may be lowered to a supine position. The process of transferring a person onto the transport apparatus is similar in reverse. Namely, when a person is lying on a mattress of a bed, for example, a person may be rolled onto sling 40 when it is in a planar configuration on the mattress (or sling 40 may be positioned under the person). Once the sling is in position under the person, the person may be raised to a seated position and thereafter rotated so that the person's legs are positioned over the side of the mattress. Apparatus 10 then may be pushed toward the support with the links 50 disengaged so that seat support members 30 and 32 are be positioned to engage the seat section, for example, by extending into the closed loops 42a and 42b of the sling. Once the seat section is coupled to seat mounting members 30 and 32, back section 44 may be raised so that its loops 44a and 44b be may be either wrapped around the distal end 16b of arm rest 16 or slid over the ends of the links 50 and guided up to engage the distal end 16b of arm rests 16. Links 50 may then be coupled to the distal ends of seat support members 30 and 32 to thereby secure seat 18 to apparatus 10.

Figure 7:
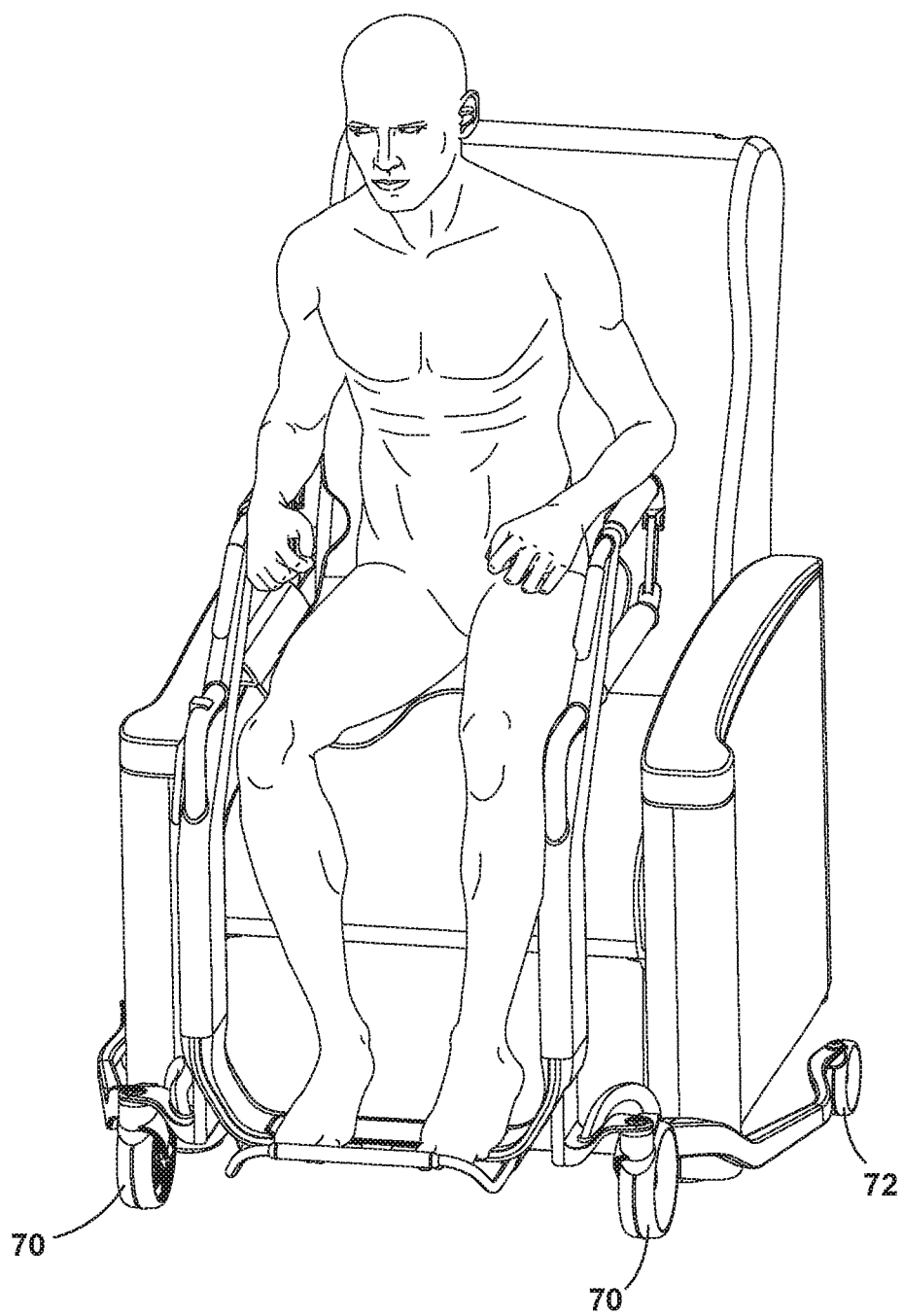
FIG. 7 illustrates the frame and the sling positioning the person over another support, such as a recliner.

Apparatus 10 may also be used as a transport apparatus to transfer the person to a chair or recliner, such as shown in FIG. 7. Depending on the construction of chair or recliner, bearings 72 may extend under the recliner or chair. Alternately, bearings 72 are mounted so that they can be separated to straddle the chair or recliner. For example, referring again to FIGS. 1 and 2, base frame members 74 may be pivotally mounted to arms 76 about pivot axes 74b to form pivot joints and allow the space between bearings 72 to be increased by rotating base frame members 74 about the distal ends of arms 76. For example, the pivot joint may incorporate a detent mechanism to define a number of preset positions for base frame members 74 so that when a force of sufficient magnitude is applied to base frame members 74, the base frame members will pivot and separate and move to one of their preset positions until the force is no longer applied at which point the base frame members will be releasably locked in place. Further, the pivot joints allow base frame members to be folded to reduce the size of the base, for storage or to improve maneuverability. When the base foot print is reduced, the frame may incorporate one or more lateral reinforcing cross-frame members between its side frame members to improve stability. For example, the lateral reinforcing cross-frame member(s) may be incorporated into the frame or may be removable. Further, the lateral reinforcing cross-frame member(s) may be deployed, for example, from a stowed position in one or both of the side frame members or can be provided as an accessory to be added as needed. When removable, the reinforcing cross-frame members may be mounted by brackets, clips, fasteners, snap-fit connections or the like.

Figure 8:
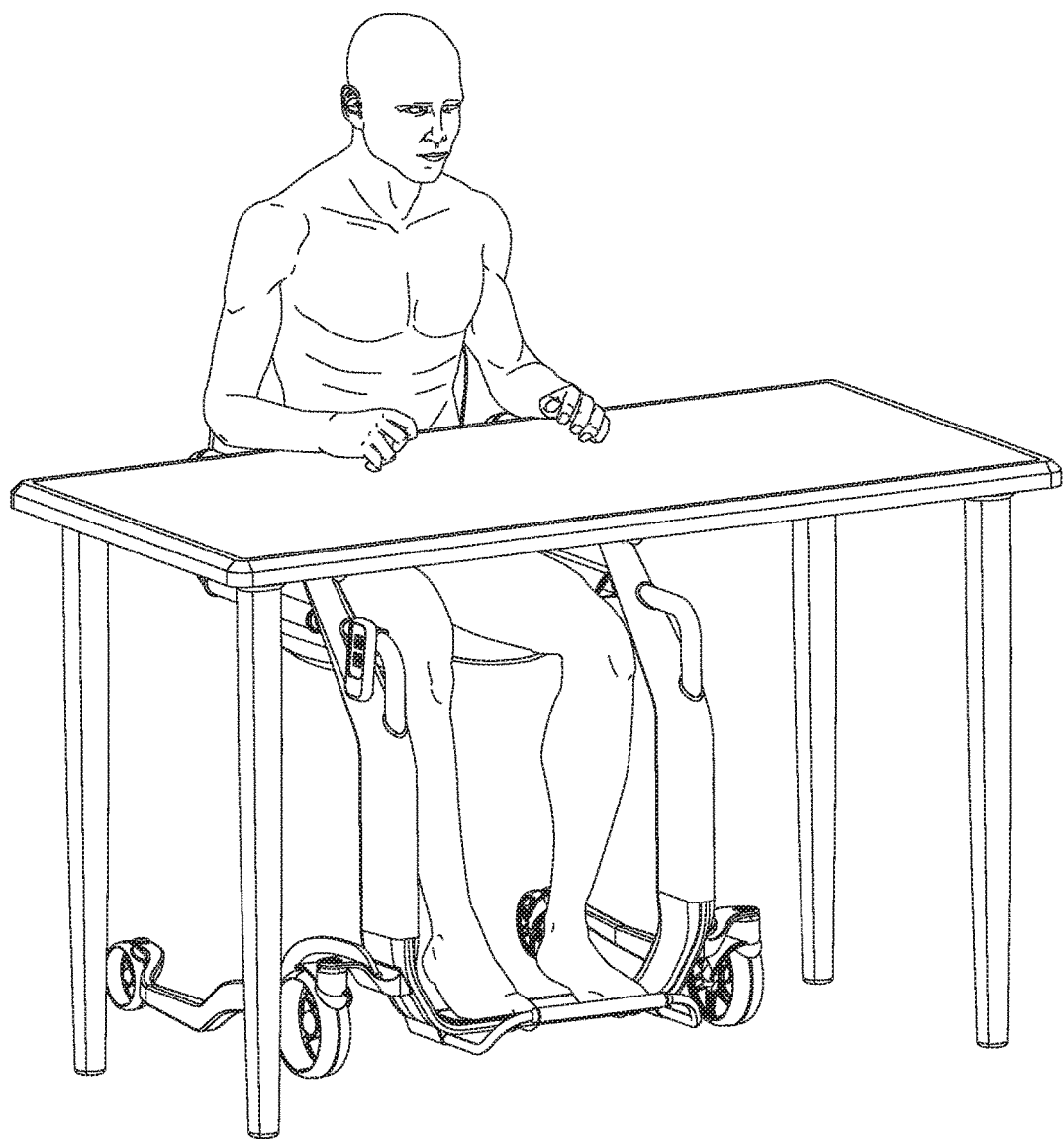
FIG. 8 illustrates the transport apparatus with a sling positioned for use adjacent a work surface, such as a table.
Figure 9:
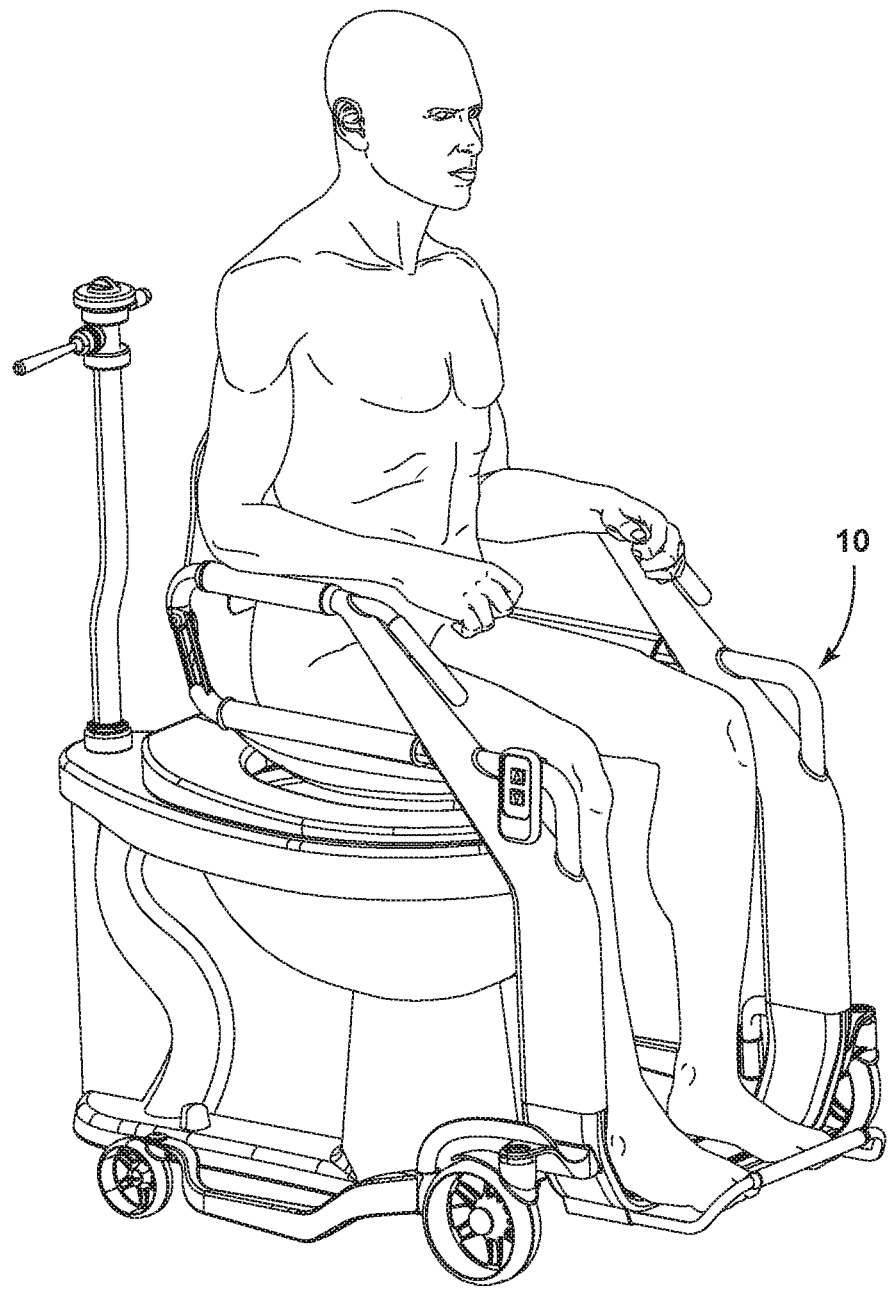
FIG. 9 illustrates the transport apparatus with a sling positioned for use with a commode.

Similarly, apparatus 10 can also be used as a chair, such as shown in FIG. 8. The height of seat 18 may be adjusted to accommodate, for example, a desk, table (FIG. 8), or other work surface. Referring to FIG. 9, apparatus 10 may be used to transport and support person while using a commode. To that end, sling 40 may be configured with an opening to allow the person to use the commode, without leaving apparatus 10.

As would be understood, therefore, the height of frame 14 relative to bearings 70, 72 can be varied. Further, referring to FIG. 10, the height of frame 14 can be adjusted so that frame 14 provides support as a walker. As best seen in FIG. 10, when sling 40 is removed, the person may stand between arm rests 16 and base members 74 and use arm rests 16 to help stabilize themselves. Optionally, handles 60 may be rotatably mounted to side frame members 24 and 26 to position their handle grips 62a inwardly to provide a more accessible gripping and/or pushing surface for the person. For example, when frame 14 is raised so that the handles are at a height suitable for engagement by a person who is standing, the person may stand between the arm rests 16 and face the access opening between side frame members 24 and 26. With their arms resting on arm rests 16, the person standing in apparatus 10 may be sufficiently stabilized by holding onto the handles so that the person may push apparatus 10 to thereby use apparatus 10 as a walker.

In addition to be used as walker, apparatus 10 may be used as a stand assist device and/or an exercise device. Many ICU patients are encouraged to attain a standing position and/or walking exercise in as short a time as possible to expedite the recovery process. Apparatus 10 enables a patient to be safely lifted into a standing position avoiding nurse back injuries. When used as a stand assist device, the seat may be configured more in the form of a sling that swings where the panel forming the sling is mounted by rings or other couplers that allow swivel at the mounting point of the sling to the frame.

Further, the driver may be used (as controlled by the control unit described above) to raise or lower the arms and/or sling while a person is using the apparatus as a walker, or is using the apparatus just to simply stand, to increase or decrease the load on a person's appendages, such as legs for rehabilitation purposes. For example, a patient recovering from knee surgery will benefit from this feature. Further, when used as a walker, for example during rehabilitation, a nurse can follow and reposition the sling into a seat configuration if needed when the person becomes fatigued.

Figure 12:
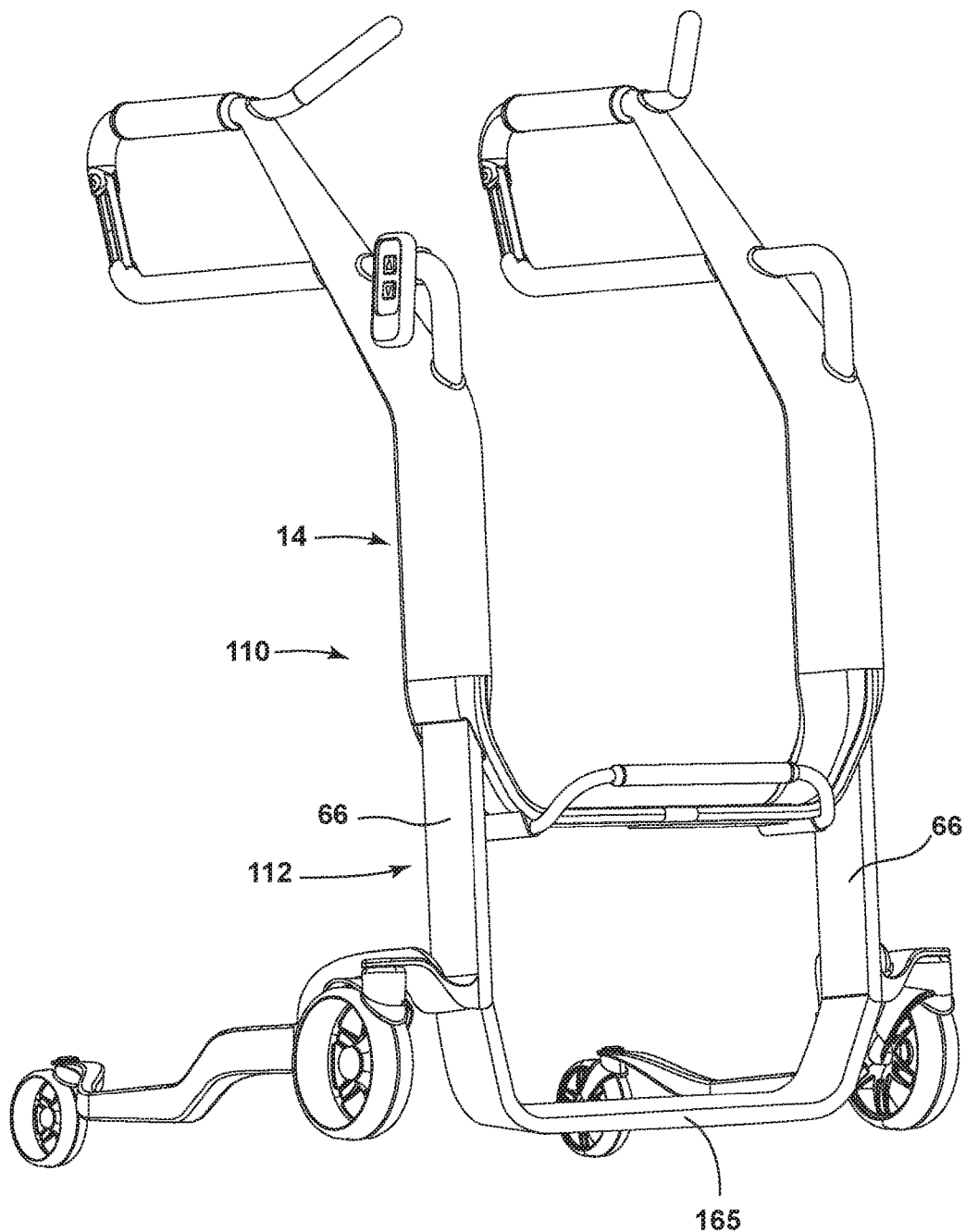
FIG. 12 is a perspective view of another embodiment of a transport apparatus.
Figure 13:
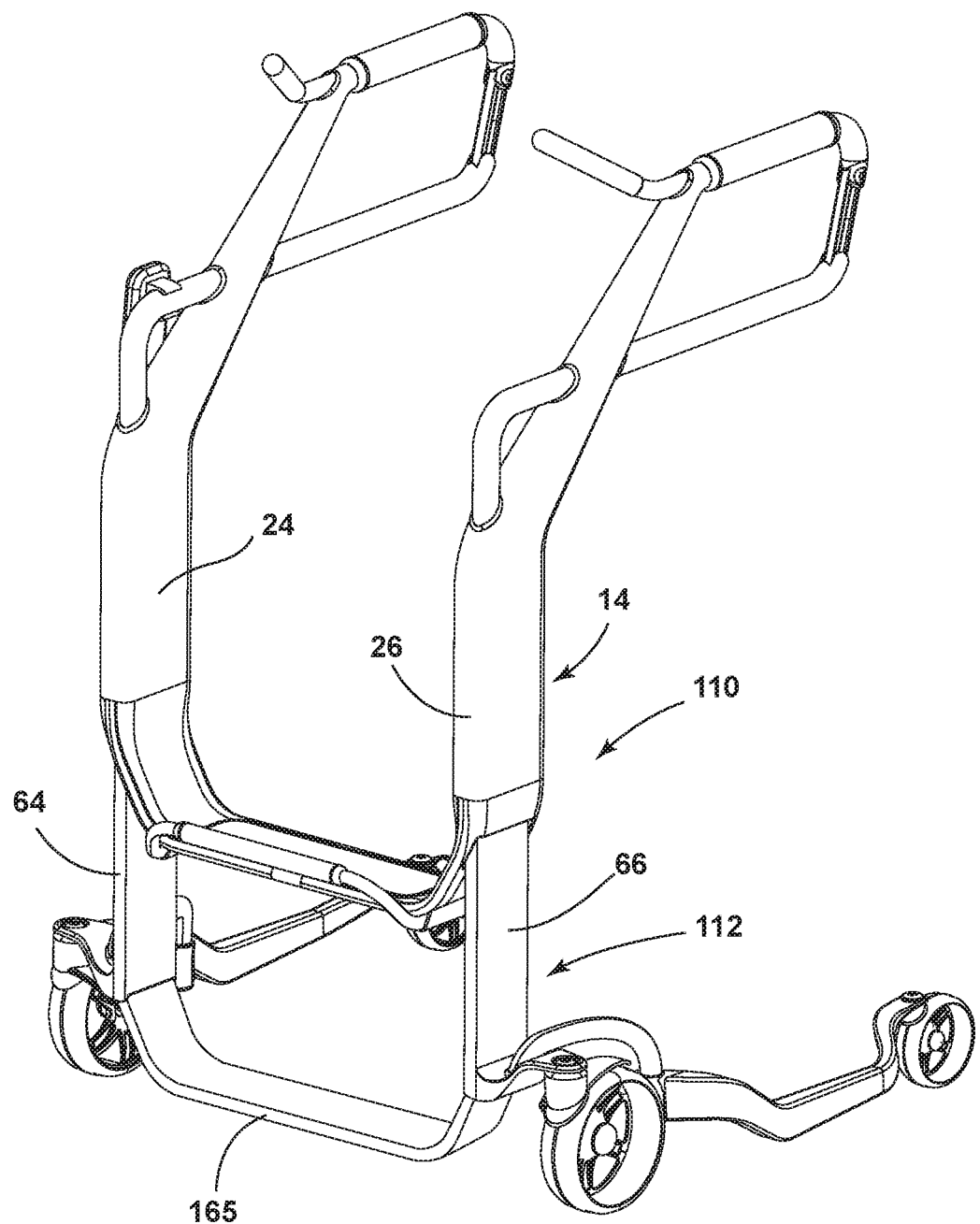
FIG. 13 is another perspective view of the transport apparatus.

Referring to FIG. 12, the numeral 110 generally designates another embodiment of a transport apparatus. Transfer apparatus 110 is a similar construction to apparatus 10 and includes frame 14 as described above and a modified base 112, which is similar to base 12, but includes a cross-frame member 165 that joins members 64 and 66 to form a U-shaped frame similar to frame 14. For example, cross-frame member 165 may be welded or otherwise secured the respective members 64 and 66 of frame 14. In this manner, apparatus 110 includes two telescoping U-shaped frames. Further in this manner, the two sides of the base 112 are joined to form a unitary base. Also, apparatus 110 may include a seat, similar to seat 18.

Figure 14:
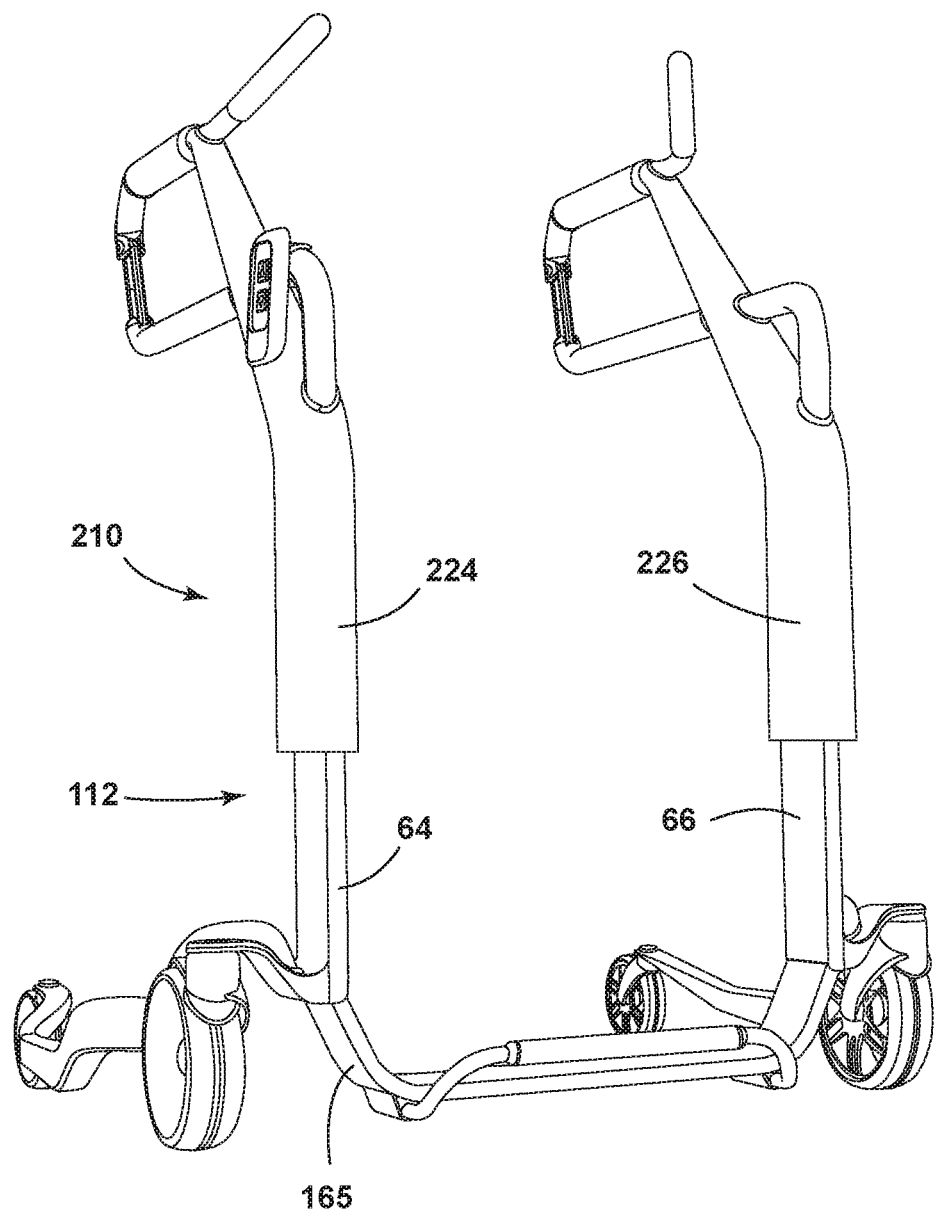
FIG. 14 is a perspective view of yet another embodiment of a transport apparatus.
Figure 15:
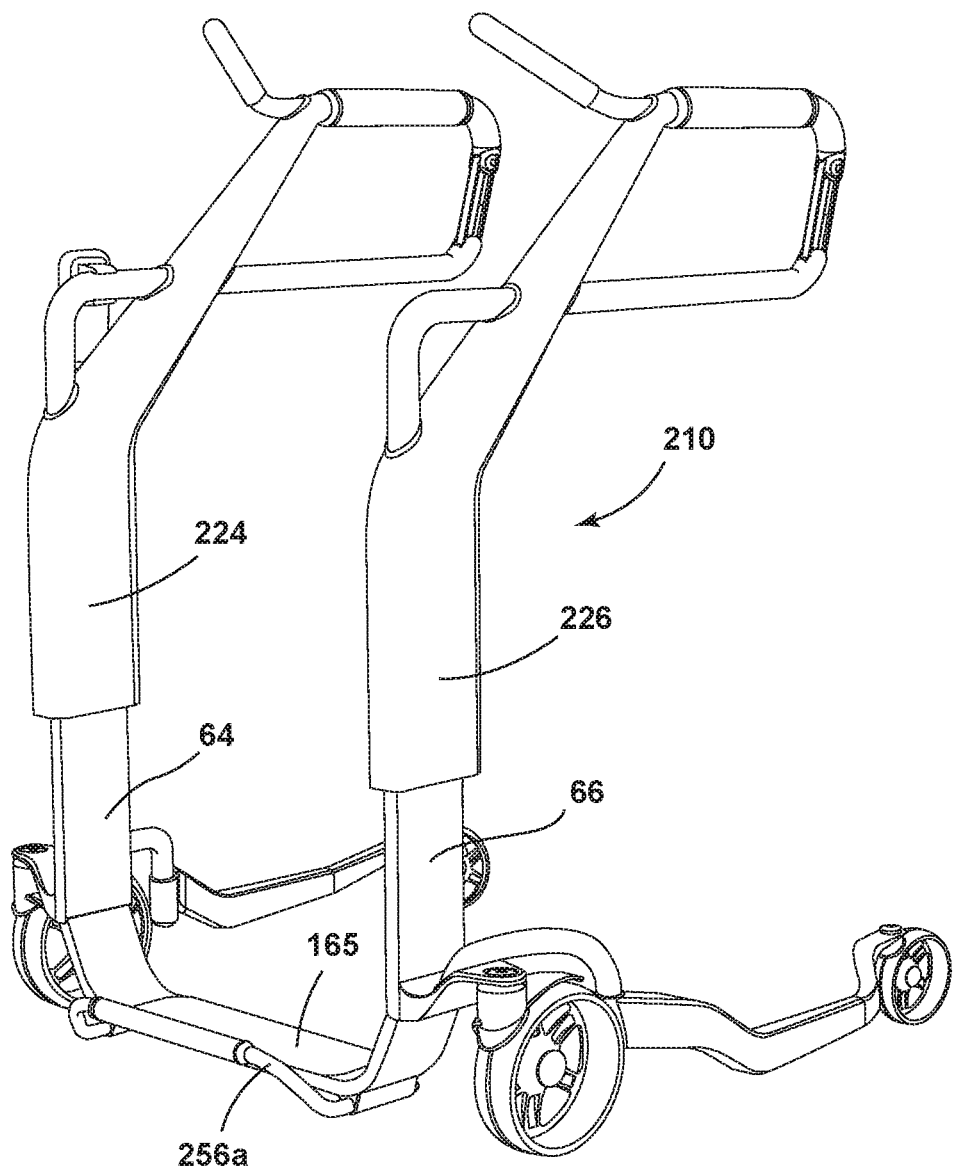
FIG. 15 is another perspective view of the transport apparatus.

Alternately as shown in FIGS. 14 and 15, apparatus 210 includes base 112 but includes disconnected columns formed by side frame members 224 and 226, which are similar to side frame members 24 and 26 but no longer joined by cross-frame member 22. In this embodiment, cross-frame member 165 of base 112 may support a footrest 265a, formed, for example, from a U-shaped tubular member which is mounted to cross-frame member 165. The tubular member forming footrest 265a may be mounted, for example, in sleeves formed at or mounted to the underside of cross-frame member 165. For further details of the construction of the common components of apparatuses 110 and 210, reference is made to the first embodiment.

Figure 16:
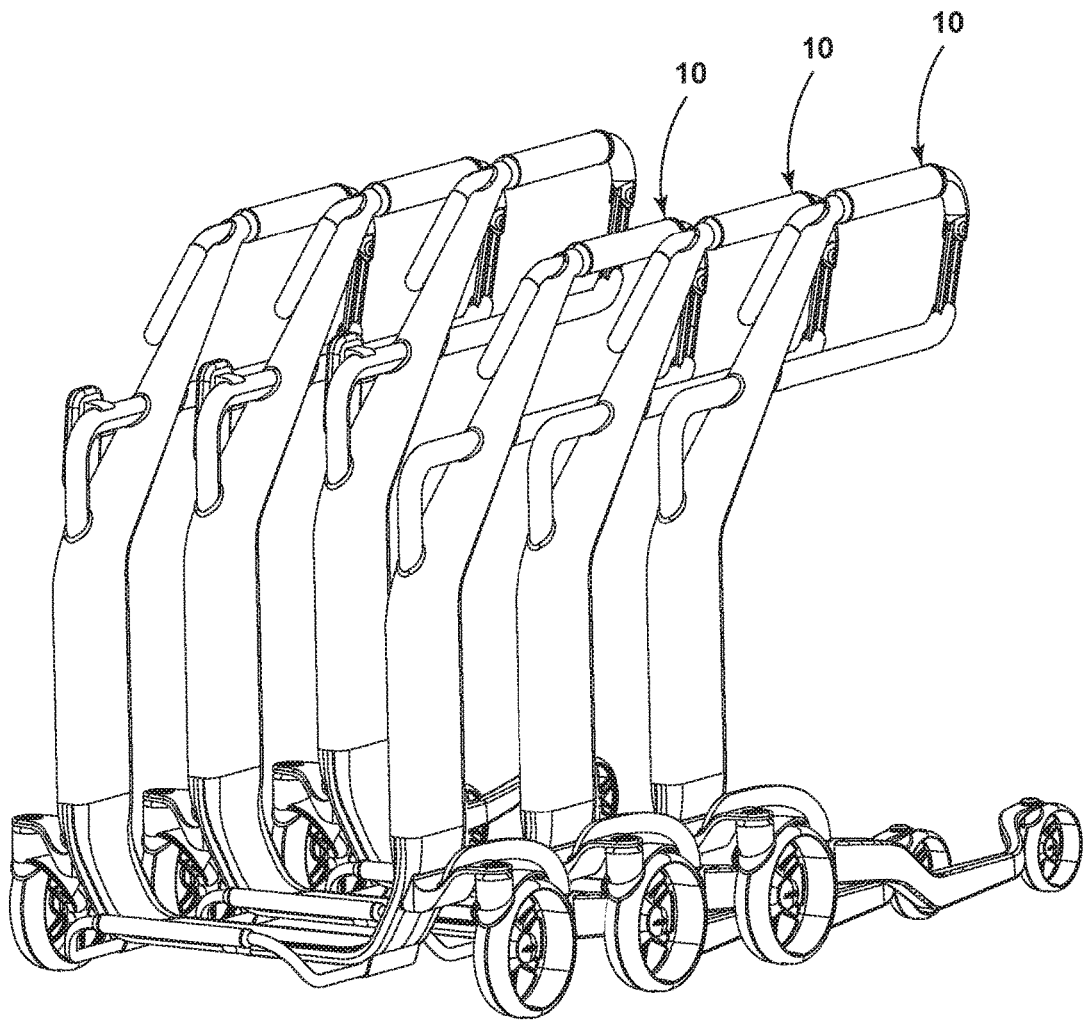
FIG. 16 illustrates three units of transport apparatuses with the sling removed and shown in a nested arrangement.

As best seen in FIG. 16, apparatus 10 (as well as apparatuses 110, 210, or 310 described below) can be configured so that it can nest with one or more apparatuses. For example, base frame members 74 are sized and optionally angled so that bearings 72 can pass under frame 14 between bearings 70. Alternately, base frame members 74 are sized and angled so that bearings 72 can straddle or go around bearings 70. Similarly, frames 14, arm rests 16, and seat mounting members 30 and 32 are sized and optionally angled so that when the base 12 of an apparatus is nested with another apparatus, the frame, the arm rests and seat mounting members 30 and 32 will also nest to allow the apparatuses to be stored in a more compact arrangement.

Figure 18:
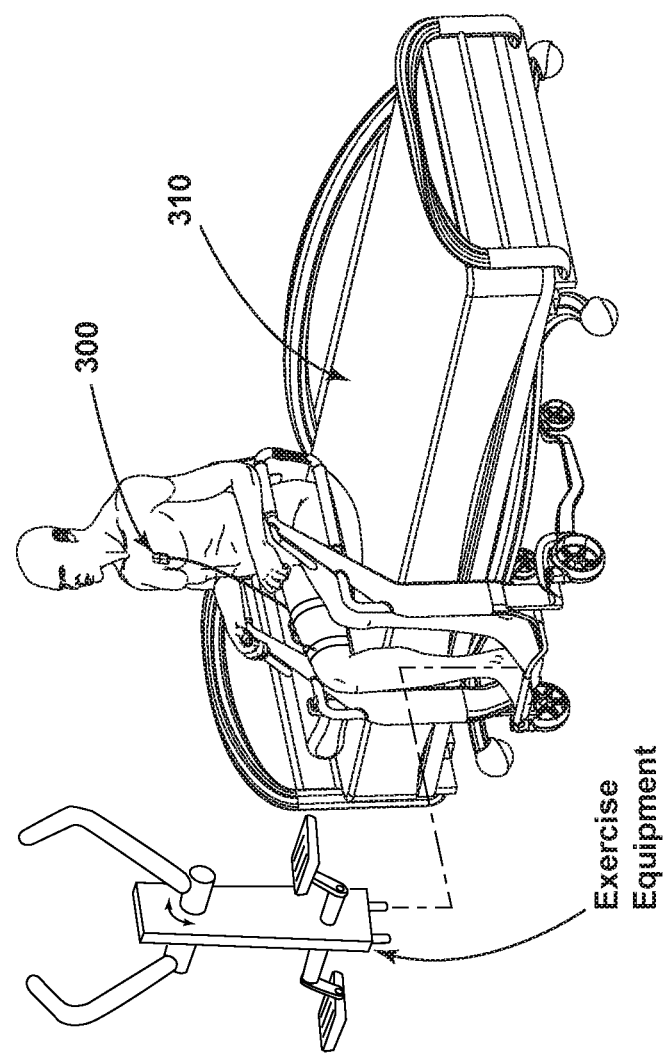
FIG. 18 is another perspective view of the transport apparatus of FIG. 17 shown adjacent exercise equipment.
Figure 17:
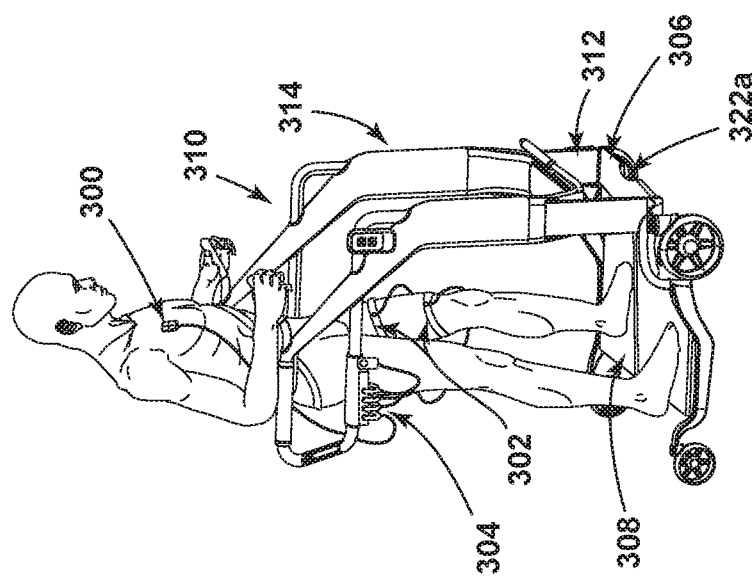
FIG. 17 is a perspective view of another embodiment of a transport apparatus.
Figure 19:
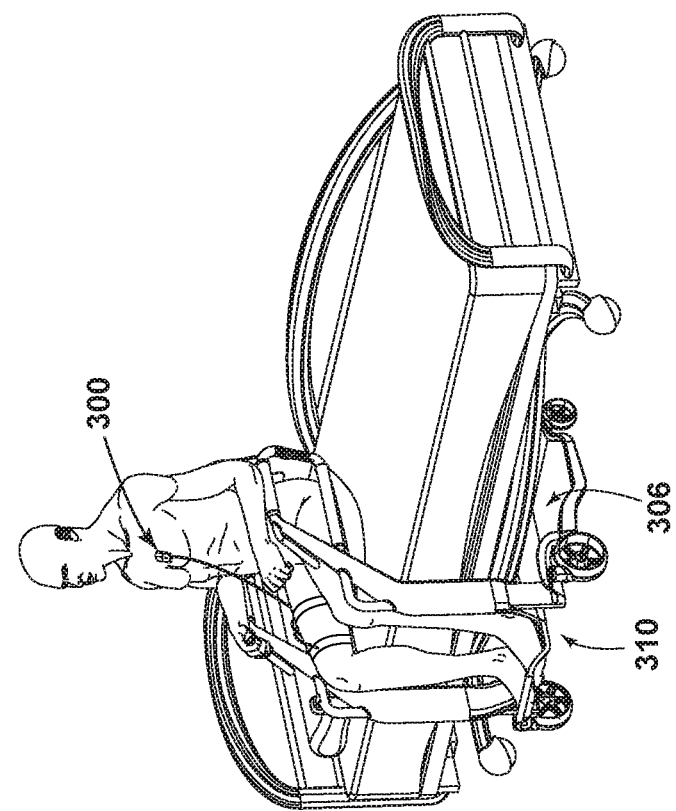
FIG. 19 is a similar view to FIG. 18 with the exercise equipment removed.

Referring to FIGS. 17-19, another embodiment of an apparatus 310 is illustrated. Apparatus 310 may be of similar construction to the previous embodiments but includes some additional features. Like apparatuses 10, 110, and 210, apparatus 310 may be employed in a number of different ways. For example, in addition to providing features for transport, stand assist, and walking, the apparatuses can support a patient while accommodating a variety of exercise equipment and therefore may also be used to support a patient while exercising, including using foot pedals or arm pedals of an exercise equipment such as shown in FIG. 18. For "In-room" physical or occupational therapy, nurses find it difficult to have patients exercise at the side of the bed because they need to provide support to the patient's back. The seat or sling feature can support the patient's back while the patient, for example, is engaged with an arm or leg exerciser, or both.

In addition, in the illustrated embodiment, apparatus 310 includes a sensor 300, which can measure a person's biometrics, such as heart rate, respiration, SpO2 and exercise time. Sensor 300 may be powered from the apparatus based power supply and optionally controlled by the control unit described above, or may be externally powered and controlled from a wall outlet and an independent control unit, or be powered by its own onboard battery and have its own controls.

Referring to FIG. 17, apparatus 310 also may include one or more electro-muscle stimulators 302. For example, in the illustrated embodiment, each electro-muscle stimulator 302 comprises a strap with one or more electrodes. The electrodes are electrically coupled to a device that generates electric impulses that induce muscle contractions when the electrodes are mounted to a person's skin by way of the straps. Alternately, the stimulators may include adhesive pads with one or more electrodes. For example, the stimulators may include control units 304 mounted to the apparatus, such as at or in the frame, or may be controlled by electronics housed in the control unit described above, or have their own electronics.

Referring again to FIG. 17, apparatus 310 may include a platform 306 that is supported by base 312, for example, by foot rest 322a. Platform 306 is optionally coupled to one or more vibration generation devices that induce vibration in platform 306. The vibration generation devices are mounted to and optionally housed in base 312 so that platform may selectively generate vibration forces, which can be then transferred to the patient through the patient's feet when the patient is standing or at least has their feet in contact with the platform. The vibration generation device or devices may be powered by and controlled by the onboard power supply and onboard control unit, such as the control unit described above. Alternately, the vibration generation device(s) may be independent from apparatus 310 and powered and controlled by an external power supply and control unit, and then simply coupled to the platform, for example, when in use.

Platform 306 may be formed by a plate 308 (such as a metallic or plastic plate or a hybrid plate (e.g. reinforced plastic)) and may be supported on base 312 by springs (e.g. metal or rubber springs), or may be supported by base 312 with sufficient degrees of freedom to allow the platform to vibrate to impart vibration therapy a person standing on the platform. Optionally, platform 306 may be mounted so that is can be folded when not in use so that it does not interfere with the walker function or other functions of the apparatus. Further, platform 306 may be removably mounted to the base, for example, by releasable fasteners or couplers.

The vibration therapy may be combined with electro-muscle contraction/electro-muscle stimulation therapy, and sensor 300 or additional sensors may be configured to measure the frequency/amplitude and time duration of the vibration.

Figure 20:
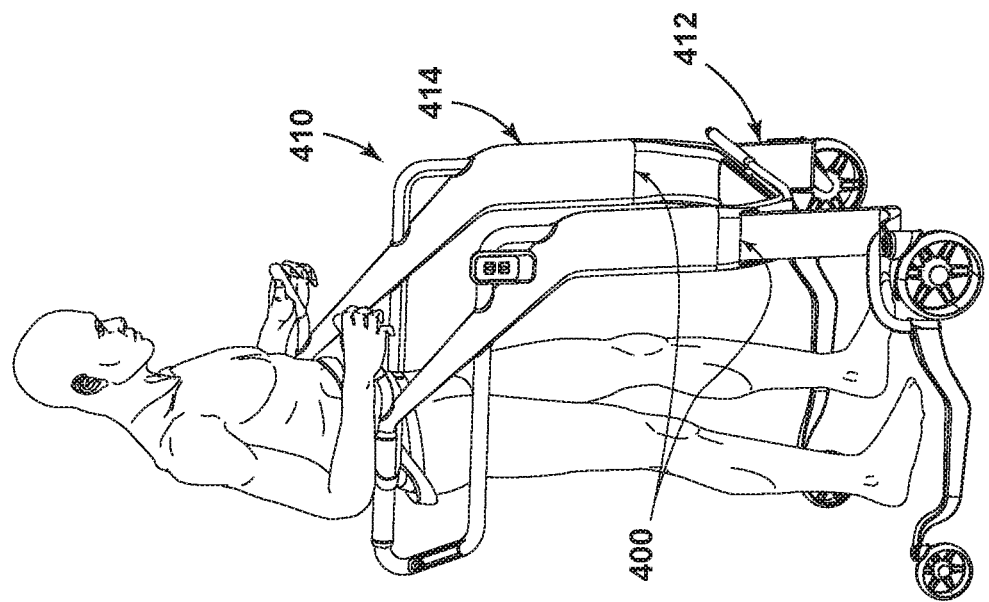
FIG. 20 is a perspective view of yet another embodiment of a transport apparatus.

Referring to FIG. 20, the numeral 410 designates yet another embodiment of a transport apparatus. Apparatus 410 may be of similar construction to the previous embodiments and includes a weigh scale, for example, in the form of load cells 400. Load cells 400 may be mounted to base 412 inside frame 414 and are arranged to weigh the load on frame 414 exerted by the person using apparatus, for example, as a walker. Alternately, load cells may be located in the arm rests. The load cells may then be in communication with the control unit described above and may be used as input, for example, as feedback, to the control unit of the lift mechanism so that the amount of force that is unloaded from the person (by the apparatus) can be determined and used to control the therapy.

Accordingly, the transport apparatuses described herein allow a person to be moved or transferred from one support, such as a bed, a stretcher, a cot, a seat, including a chair, a car seat, wheelchair, an airplane seat, or a seat on a commode, to another support. The transport apparatus may be used as a seat or used as a walker. Further, because the bearings can be configured so that they are capable of steering or so that they can have a more compact configuration (e.g. when the base is folded), apparatus 10 (or 110, 210, 310, 410) can optionally be configured to translate sideways (e.g. generally orthogonal to or in a direction angled with respect to the egress or ingress path) to allow a person to be transferred to a support that is adjacent the side of the apparatus. For example, apparatuses 10, 110, 210, 310, and 410 may be used to transfer a patient to a seat, for example, on an airplane.

As noted above, the apparatus may be equipped with a sling mounted to the upper frame, which supports the person in a sitting position. When the person is raised up to a standing position, the person's feet tend migrate to the platform in a functional vibration position as a result of the sling mounting location. Typically, in use, the sling is placed in position when the patient is in a sitting position on the bed (or other surface). When the lift is then operated, the person is raised into a standing position. Thus, by locating the vibration generation devices in the base of the unit, vibration can be applied when the person is standing. Alternately or in addition, the vibration device(s) may be coupled to the sling, for example at the sling mounts, and optionally located in or at least supported by the frame. In this manner, vibration therapy can be applied in a variety of patient positions, including the seated position.

Accordingly, the apparatuses described above provide a variety of functions alone or in combination—a stand assist function, a walking assist function, an exercise assist function, a transport or transfer function, as well as vibration therapy and/or muscle stimulation.

While reference is made herein to the various components as "members," it should be understood that this term is used broadly and may encompass a wide variety of structural elements or components, including rods, tubes, angles, plates, for example, and further typically are metal or plastic or composite structural members, such as aluminum or stainless steel or reinforced plastic or the like, though it should be understood that other materials may be used. The members may be welded together or joined by fasteners, such as removable fasteners or the like. Further, some members may be molded or die cast together. Additionally, each member may be formed from one or more components; therefore the term member is used broadly and not intended to be limited to a single component. Additionally, while several components have been described as separate members, some members may be combined.

While several forms of the invention have been shown and described, other forms will now be apparent to those skilled in the art. For example, while a sling that forms both the seat section and the back section is illustrated, it should be understood that separate seat and back sections may be provided. Further, the frames may have a fixed height.

It also should be understood that in any of the embodiments described herein, the footprint of the respective apparatus may be increased or decreased depending on the application. For example, for home use, the transport apparatus may be configured to have a footprint that clears standard doorways. Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

The embodiments of the invention in which we claim an exclusive property right or privilege is claimed are defined as follows:

1. A transport apparatus comprising:
    a movable wheeled base, said wheeled base including two spaced apart base members, each of said base members supporting front and rear bearings;
    an inverted U-shaped frame comprising:
    a pair of spaced columns;
    a foot rest at a lower end thereof;
    first and second spaced apart seat support members supported by said columns and configured to support a seat for supporting a person thereon; and
    said U-shaped frame mounted relative to said base wherein said foot rest extends between said base members, said columns being configured to extend wherein said seat support members move from a first position spaced relative to said base to a second position spaced relative to said base, said U-shaped frame forming an access opening between said columns and said seat support members and above said foot rest, said access opening being free of any obstructions wherein said access opening allows a person egress and ingress between said columns and said seat support members to and from the seat when the seat is supported by said seat support members, and said base being free of obstructions between said base members to allow egress and ingress between said base members and said bearings so that when the seat is removed from said transport apparatus a person may stand between said base members and said seat support members and use said transport apparatus as a walker.

2. The transport apparatus according to claim 1, in combination with a seat, and said seat being configured to be supported by said seat support members.

3. The transport apparatus according to claim 2, wherein said seat includes a seat portion and a back portion, said seat portion and said back portion are connected together and are reconfigurable between an unfolded, generally planar configuration wherein said seat can lie generally flat on a support surface so that a person may be moved onto said seat and a folded configuration wherein a person can be supported in a sitting position on said seat.

4. The transport apparatus according to claim 3, wherein said seat portion of said seat is releasably engageable with said seat support members.

5. The transport apparatus according to claim 4, wherein said back portion is releasably engageable with said columns to hold said seat in its folded configuration.

6. The transport apparatus according to claim 2, wherein said seat includes a pair of sleeves, said seat support members being extendible into said sleeves to thereby mount said seat to said frame.

7. The transport apparatus according to claim 6, further comprising an extended footrest mounted to said U-shaped frame.

8. The transport apparatus according to claim 2,
said seat comprising a flexible panel being reconfigurable between an unfolded, generally planar configuration wherein said panel can lie generally flat on a support surface so that a person may move or be moved onto said panel and a folded configuration wherein a person can be supported in a sitting position on said panel.

9. The transport apparatus according to claim 8, wherein each of said side frame members supports a mount for releasably mounting said seat to said side frame members.

10. The transport apparatus according to claim 9, wherein portions of said side frame members form arm rests.

11. The transport apparatus according to claim 10, wherein said arm rests, said mounts, and said side frame members form closed loops.

12. The transport apparatus according to claim 10, wherein each of said arm rests and each of said mounts are joined by a releasable link, when released said links open said closed loops to thereby allow said panel to be removed from said frame.

13. The transport apparatus according to claim 8, wherein said forward bearing and rearward bearings comprise forward wheels and rearward wheels.

14. The transport apparatus according to claim 13, wherein said frame is mounted between said forward wheels.

15. The transport apparatus according to claim 13, wherein said forward wheels and said rearward wheels define a footprint, and when said seat is mounted to said frame, said seat is supported within said footprint.

16. The transport apparatus according to claim 8, wherein said frame comprises at least one driver for moving said frame relative to said bearings.

17. The transport apparatus according to claim 8, wherein said seat includes an opening to allow a user to use a commode without removal of said seat.

18. The transport apparatus according to claim 1 further comprising a driver operative to raise or lower said frame relative to the base.

19. The transport apparatus according to claim 1, wherein said U-shaped frame include lower portions and upper portion, said lower portions extending vertically, and said upper portions angled or curved with respect to said lower portions, and said seat support members extending from at least said upper portions.

20. The transport apparatus according to claim 19, wherein said seat support members comprise L-shaped members extending from said lower portions and through said upper portions.

\* \* \* \* \*